(12) United States Patent
Sato

(10) Patent No.: US 10,197,386 B2
(45) Date of Patent: Feb. 5, 2019

(54) BEND INFORMATION COMPUTATION APPARATUS

(71) Applicant: OLYMPUS CORPORATION, Tokyo (JP)

(72) Inventor: Ken Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/991,022

(22) Filed: May 29, 2018

(65) Prior Publication Data

US 2018/0274907 A1 Sep. 27, 2018

Related U.S. Application Data

(63) Continuation of application No. PCT/JP2015/083643, filed on Nov. 30, 2015.

(51) Int. Cl.
*G01B 11/16* (2006.01)
*A61B 1/00* (2006.01)
(Continued)

(52) U.S. Cl.
CPC ............... *G01B 11/16* (2013.01); *A61B 1/00* (2013.01); *A61B 1/00165* (2013.01);
(Continued)

(58) Field of Classification Search
CPC .... A61B 2034/2055; A61B 2034/2061; A61B 34/20; A61B 1/00; A61B 1/005;
(Continued)

(56) References Cited

U.S. PATENT DOCUMENTS 4,356,396 A * 10/1982 Ruell ................... G01D 5/30
250/226
9,146,097 B2 9/2015 Fujita et al.
(Continued)

FOREIGN PATENT DOCUMENTS

JP S64-88373 A 4/1989
JP H02-290536 A 11/1990
(Continued)

OTHER PUBLICATIONS

International Search Report dated Feb. 16, 2016 issued in PCT/JP2015/083643.

(Continued)

*Primary Examiner* — Gordon J Stock, Jr.
(74) *Attorney, Agent, or Firm* — Scully, Scott, Murphy & Presser, P.C.

(57) ABSTRACT

A bend information computation apparatus includes a light source, a first light guide, a detection target, a second light guide, a switching member, a driver, a detector, a generator, and a bend information arithmetic operator. The detector is configured to detect first and second spectrum change. The generator is configured to calculate, based on the second spectrum change, suppression information. The bend information arithmetic operator is configured to calculate change information based on the first spectrum change and the suppression information and to compute bend information based on the change information.

4 Claims, 18 Drawing Sheets

(51) Int. Cl.
*G01M 11/00* (2006.01)
*G01D 5/353* (2006.01)
*G01D 5/26* (2006.01)
*A61B 34/20* (2016.01)
*A61B 1/07* (2006.01)
*A61B 1/005* (2006.01)

(52) U.S. Cl.
CPC .............. *A61B 34/20* (2016.02); *G01D 5/268* (2013.01); *G01D 5/35367* (2013.01); *G01M 11/31* (2013.01); *A61B 1/005* (2013.01); *A61B 1/07* (2013.01); *A61B 2034/2061* (2016.02)

(58) Field of Classification Search
CPC ....... A61B 1/00165; A61B 1/07; G01B 11/16; G01B 11/18; G01M 11/30; G01M 11/31; G01M 11/3145; G01D 5/268; G01D 5/353; G01D 5/35316; G01D 5/35354; G01D 5/35358; G01D 5/35361; G01D 5/35364; G01D 5/35367; G01D 5/3537; G01D 5/35374; G01D 5/3538
See application file for complete search history.

(56) References Cited

U.S. PATENT DOCUMENTS

| | | |
|---|---|---|
| 2007/0116415 A1 | 5/2007 | Kobayashi |
| 2017/0095143 A1* | 4/2017 | Sato ........................ G02B 23/24 |
| 2017/0100196 A1* | 4/2017 | Takayama ................ A61B 1/00 |
| 2017/0239001 A1* | 8/2017 | Sato .................... A61B 1/00004 |
| 2017/0311775 A1* | 11/2017 | Fujita .................. A61B 1/00013 |
| 2018/0055336 A1* | 3/2018 | Sato ........................ A61B 1/00 |
| 2018/0084977 A1* | 3/2018 | Fujita ..................... G01B 11/24 |
| 2018/0200000 A1* | 7/2018 | Takayama ................ A61B 1/00 |
| 2018/0224269 A1* | 8/2018 | Takayama ................ A61B 1/00 |

FOREIGN PATENT DOCUMENTS

| | | |
|---|---|---|
| JP | 2002-116141 A | 4/2002 |
| JP | 2005-189217 A | 7/2005 |
| JP | 4714570 B2 | 6/2011 |
| JP | 2012-220241 A | 11/2012 |
| JP | 2015-034787 A | 2/2015 |
| JP | 2015-181495 A | 10/2015 |

OTHER PUBLICATIONS

English translation of International Preliminary Report on Patentability dated Jun. 14, 2018 together with the Written Opinion in related International Application No. PCT/JP2015/083643.

\* cited by examiner

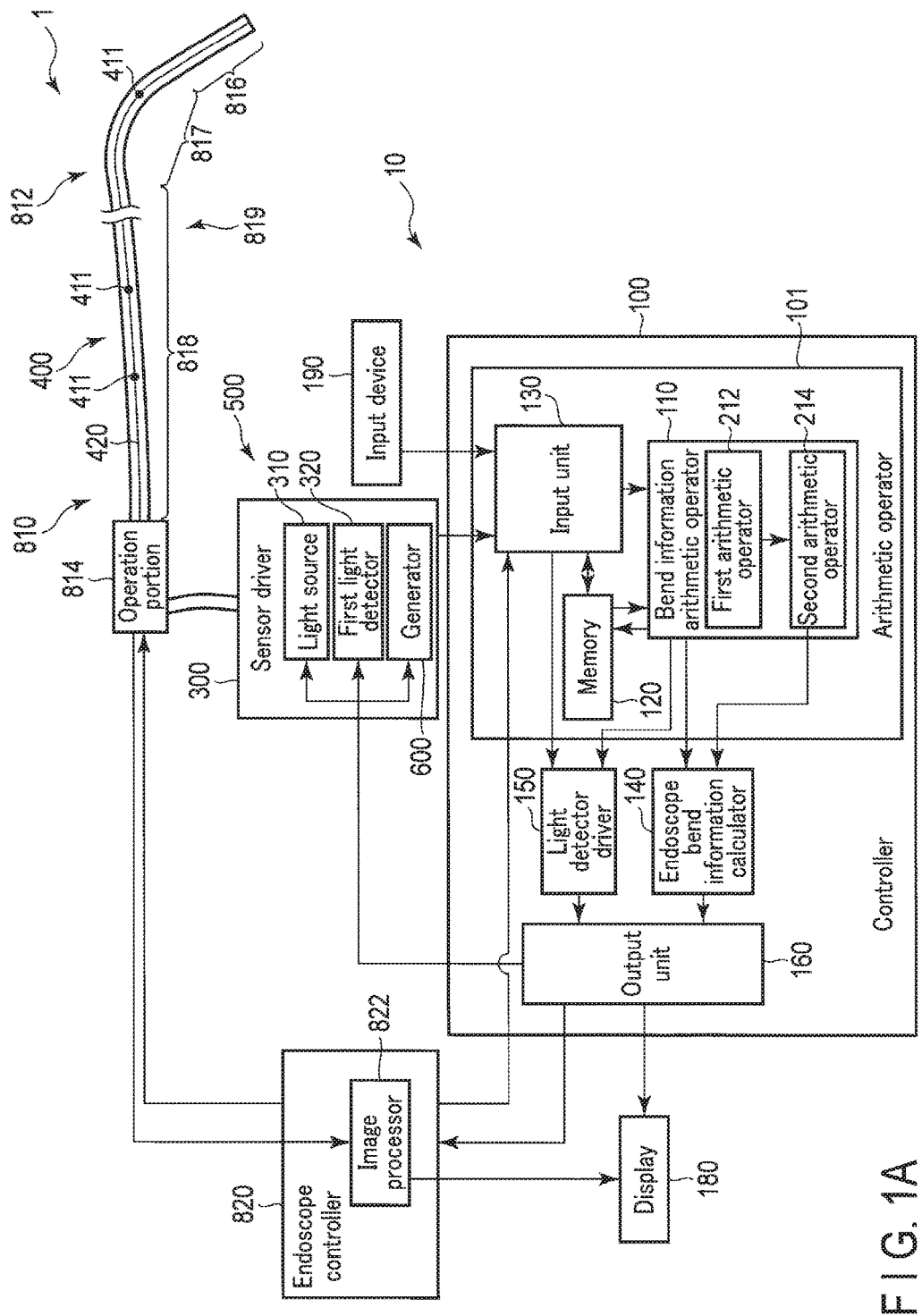
F I G. 1A

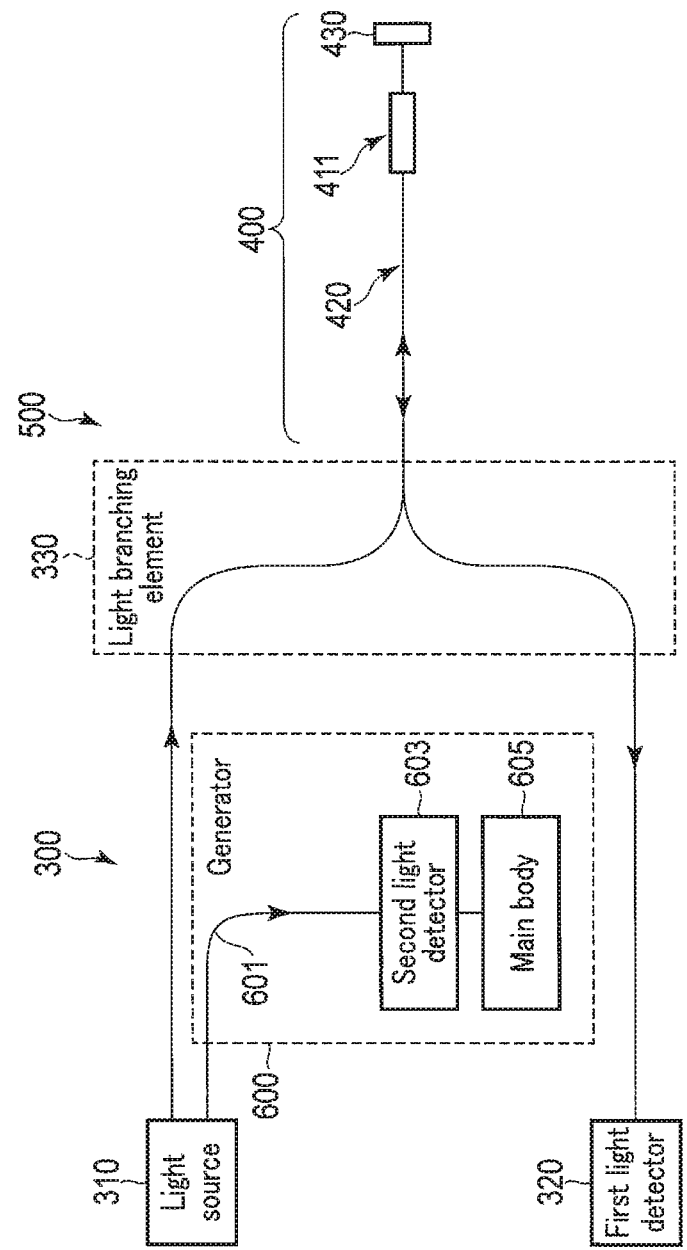
F I G. 2

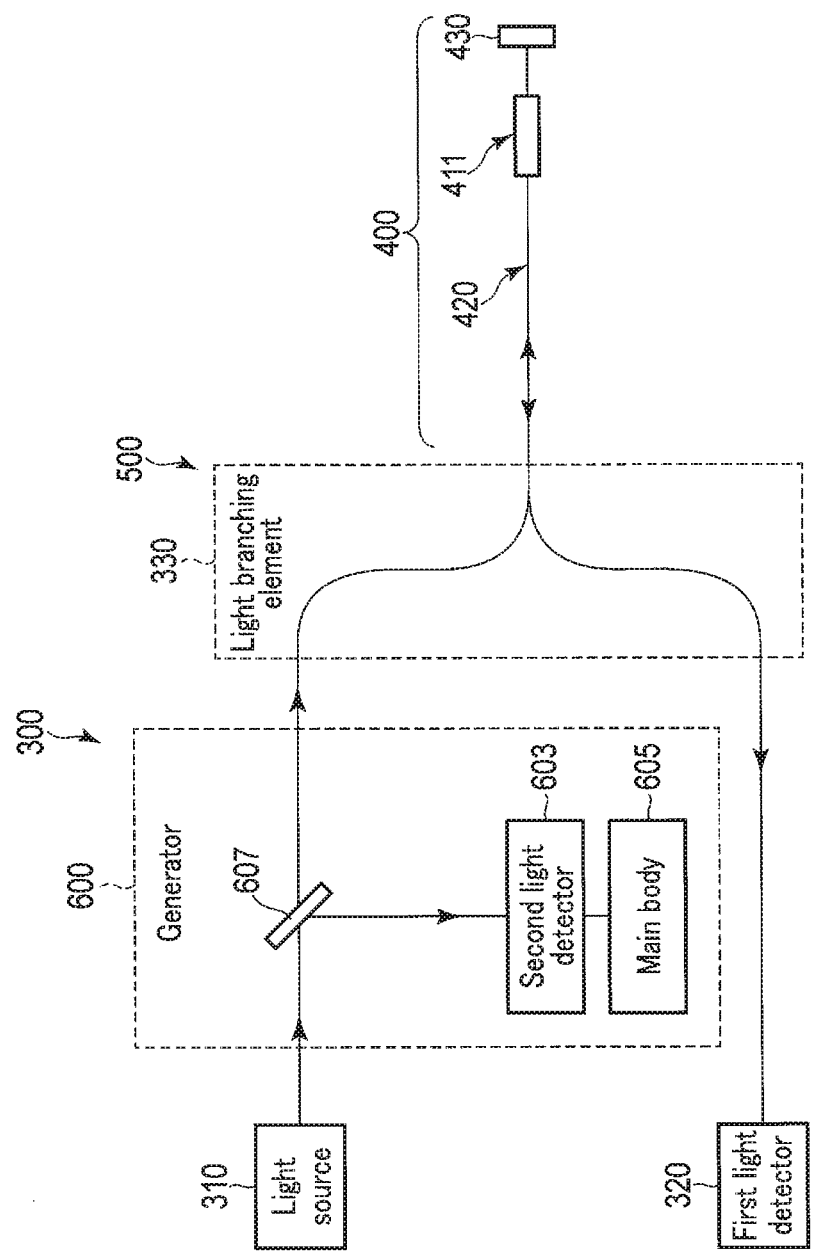
F I G. 11

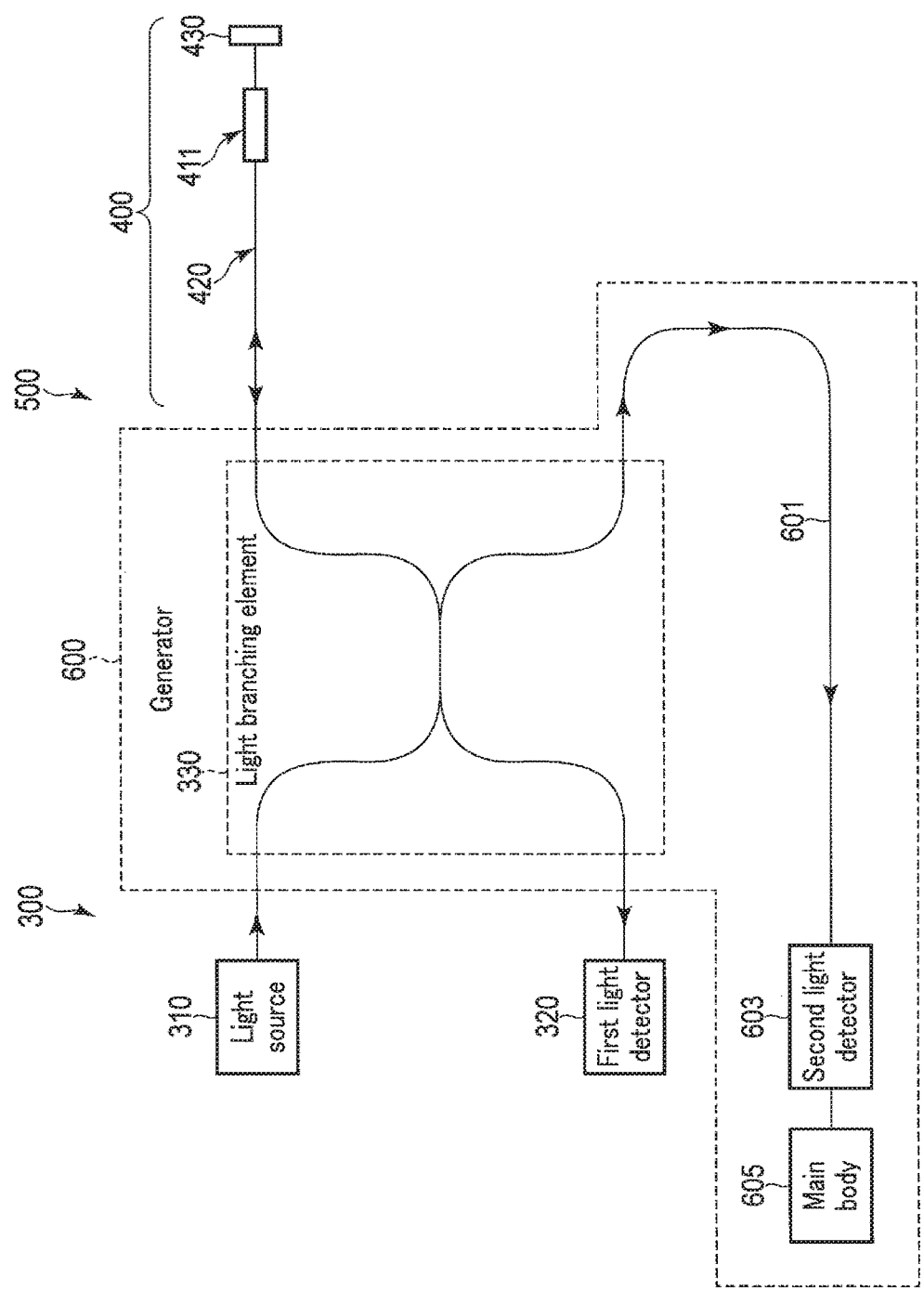
F I G. 12

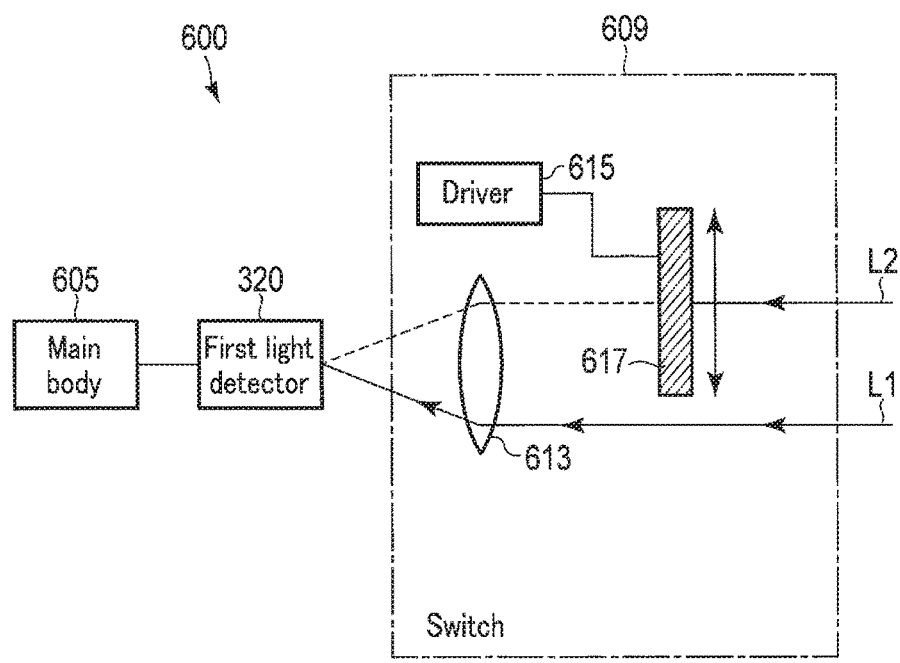
F I G. 14A
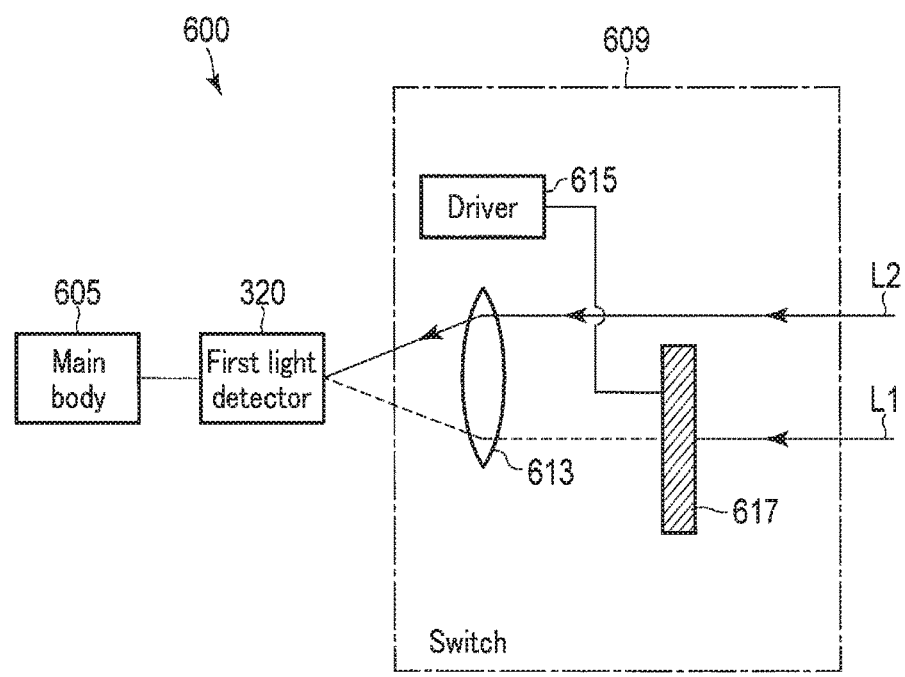
F I G. 14B

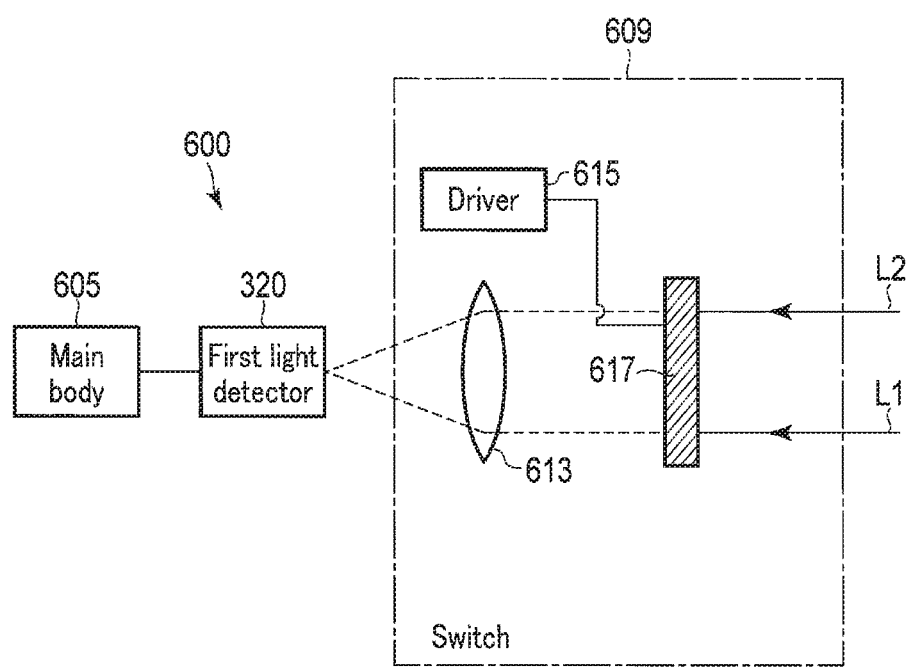
F I G. 14C

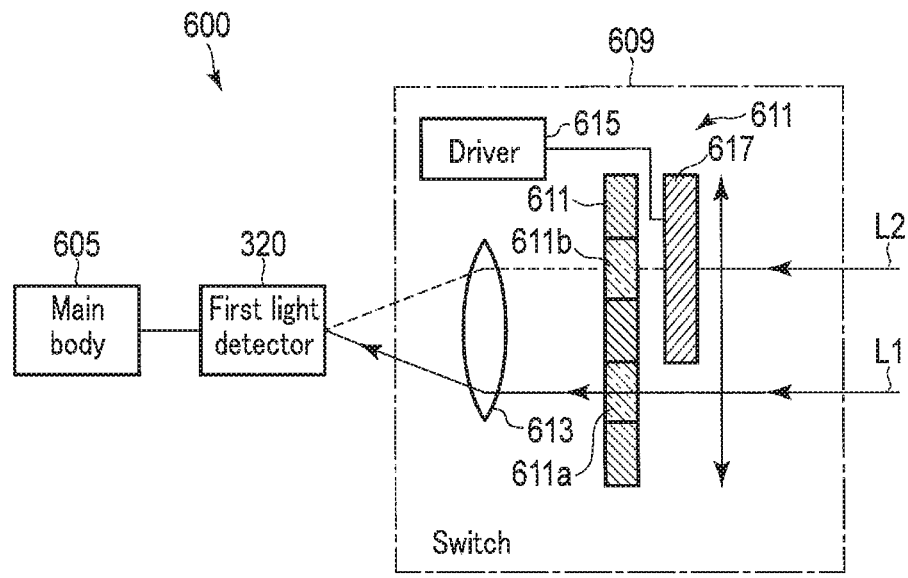
F I G. 15A
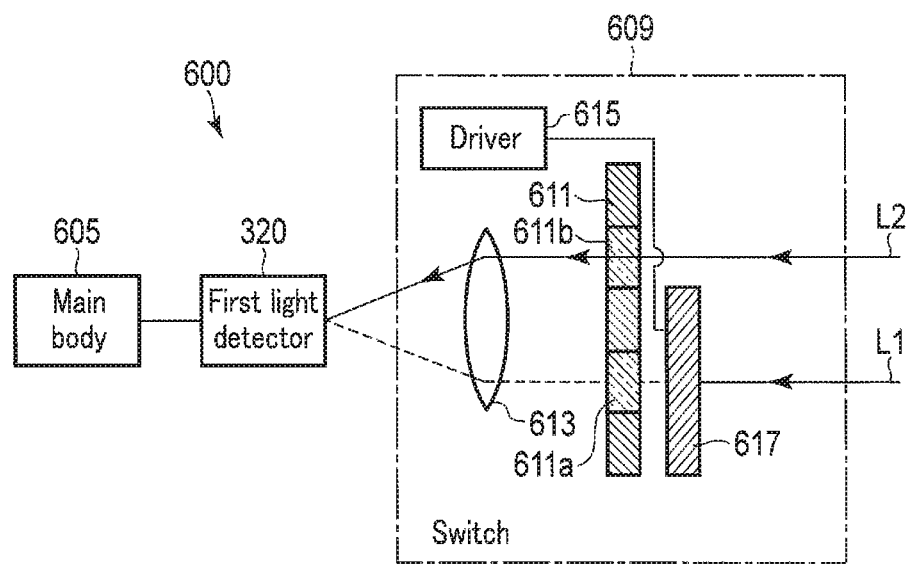
F I G. 15B

BEND INFORMATION COMPUTATION APPARATUS

CROSS-REFERENCE TO RELATED APPLICATIONS

This application is a Continuation Application of PCT Application No. PCT/JP2015/083643, filed Nov. 30, 2015, the entire contents of all of which are incorporated herein by references.

BACKGROUND OF THE INVENTION

1. Field of the Invention

The present invention relates to a bend information computation apparatus for computing bend information that represents a bend state of a flexible portion having flexibility.

2. Description of the Related Art

An apparatus that is incorporated in a flexible insertion portion of an insertion apparatus (for example, an endoscope) for detecting a bend state of an insertion portion has been known. For example, Japanese Patent No. 4714570 discloses an endoscope shape-detecting probe using an optical fiber. This probe is provided with an optical fiber that bends together with the insertion portion. The optical fiber is provided with two optical modulators at approximately the same positions with respect to a longitudinal direction of the optical fiber. The first optical modulator may detect, for example, a curvature in the X direction, and the second optical modulator may detect a curvature in the Y direction that is orthogonal to the X direction. Each of the optical modulators may modulate the intensities of the wavelength components of the light that is transmitted through the optical fiber. In this probe, the curvature of the optical fiber at the optical modulators and also the curvature of the insertion portion that is bent along with the optical fiber are detected, based on the intensities of the wavelength components before and after passing through the optical modulators.

BRIEF SUMMARY OF THE INVENTION

A bend information computation apparatus according to an embodiment of the present invention includes a light source configured to emit light; a first light guide configured to guide first light which is part of the light; a detection target provided in the first light guide and having influence on a spectrum of the first light that is guided by the first light guide; a second light guide configured to guide second light which is part of the light and is different from the first light; a switching member including a first transmission portion having a predetermined first light transmittance, a second transmission portion having a second light transmittance different from the first light transmittance, and a light shield portion, wherein the first light guided by the first light guide and the second light guided by the second light guide travel to the switching member; a driver configured to drive the switching member and thereby switch between a first state and a second state, wherein, in the first state, the first transmission portion is positioned on an optical path of the first light to allow the first light to transmit through, and the light shield portion is positioned on an optical path of the second light to shield the second light; and in the second state, the light shield portion is positioned on the optical path of the first light to shield the first light, and the second transmission portion is positioned on the optical path of the second light to allow the second light to transmit through; a detector configured to detect a first spectrum change and a second spectrum change, wherein the first spectrum change is a change in the spectrum of the first light that has transmitted through the first transmission portion in the first state, and the second spectrum change is a change in a spectrum of the second light that has transmitted through the second transmission portion in the second state; a generator configured to calculate, based on the second spectrum change, suppression information to suppress influence of a change in a spectrum of the light source on the first spectrum change; and a bend information arithmetic operator configured to calculate change information based on the first spectrum change and the suppression information and to compute bend information representing a bend direction and a bend magnitude of the first light guide based on the change information, wherein the change information represents a spectrum change in which the influence of the change in the spectrum of the light source on the first spectrum change is suppressed.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 1A is a diagram schematically showing a configuration of an endoscope system incorporating a bend information computation apparatus according to a first embodiment of the present invention.

FIG. 2 is a block diagram showing an example configuration of a sensor.

FIG. 11 is a block diagram showing an example configuration of a sensor according to a first modification of the first embodiment.

FIG. 12 is a block diagram showing an example configuration of a sensor according to a second modification of the first embodiment.

FIG. 14A is a diagram showing a first modification of the second embodiment, in which a light shielding member is in the first state.

FIG. 14B is a diagram showing the light shielding member of FIG. 14A in the second state.

FIG. 14C is a diagram showing that the light shielding member of FIG. 14A in the third state.

FIG. 15A is a diagram showing a second modification of the second embodiment, in which the light shielding member is in the first state.

FIG. 15B is a diagram showing the light shielding member of FIG. 15A in the second state.

DETAILED DESCRIPTION OF THE INVENTION

Figure 1B:
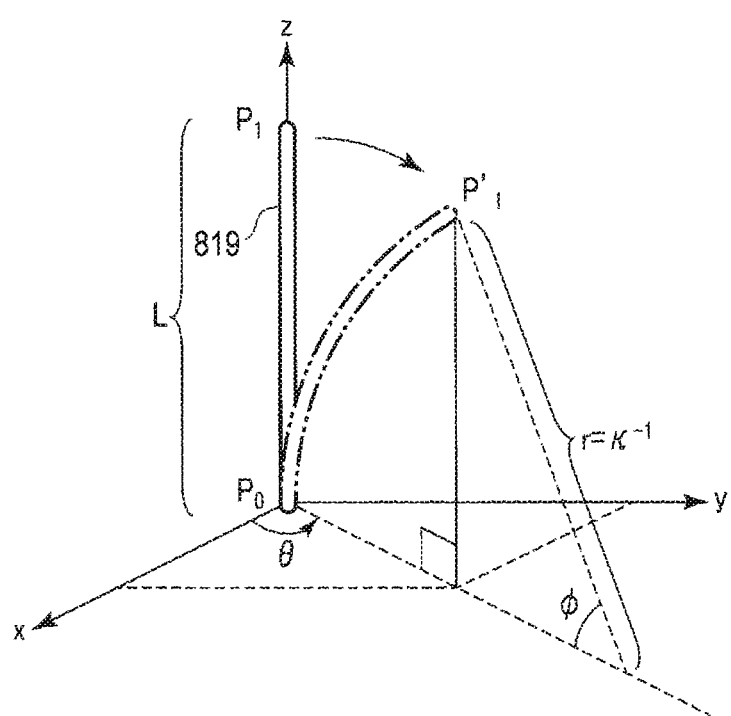
FIG. 1B is a diagram explaining a magnitude indicating a bend state of a flexible portion.

Hereinafter, embodiments of the present invention will be described in detail with reference to the drawings. Part of the components may be omitted from some drawings for clarity of the illustration.

First Embodiment

The first embodiment will be described below.

As shown in FIG. 1A, the endoscope system 1 includes an endoscope 810, an endoscope controller (endoscope control portion) 820, an input device 190, a display (display portion) 180, and a bend information computation apparatus (hereinafter referred to as a computation apparatus 10).

The endoscope 810 according to the present embodiment is an example of an insertion apparatus to be inserted into an insertion target. Examples of insertion apparatuses may include, besides the endoscope 810, a catheter and a treatment tool. The endoscope 810 will be described as a flexible endoscope for medical use, but is not limited to this. The endoscope 810 may be, for example, a flexible endoscope for industrial use. The endoscope 810 that serves as an insertion apparatus should be provided with a flexible insertion portion 812 to be inserted into the insertion target. The insertion target is not limited to a person, but may be an animal, or any other structure.

The endoscope 810 includes an insertion portion 812 to be inserted into the insertion target, an operation portion 814 connected to a proximal end portion of the insertion portion 812 to operate the endoscope 810, and a cord (not shown in the drawings) attachable to and detachable from the endoscope controller 820.

The insertion portion 812 may be hollow and elongated. The insertion portion 812 includes a hard end portion 816, a bendable portion 817, and a flexible tube 818 arranged in this order from a distal end portion of the insertion portion 812 to a proximal end portion of the insertion portion 812. Various internal components are provided inside the hard end portion 816, depending on the use of the endoscope 810. The internal components may include a not-shown illumination optical system and a not-shown image sensor (for example, a CCD). The bendable portion 817 can bend for a desired amount in a desired direction in response to the operation of the operation portion 814. The flexible tube 818 has flexibility, and is bendable by an external force.

The insertion portion 812 may be tubular, flexible, and elongated. The insertion portion 812 can actively bend in response to the operation of the operation portion 814.

Furthermore, when receiving an external force, the insertion portion 812 can be also passively bent by the external force. The insertion portion 812 inserted into the insertion target can be bent in accordance with the internal shape of the insertion target.

The operation portion 814 is employed for various operations of the endoscope 810 including the bendable portion 817.

The endoscope controller 820 controls the operations of the endoscope 810 such as driving the image sensor and adjusting the illumination light. The endoscope controller 820 includes an image processor (image process portion) 822 that processes images acquired by the image sensor. The endoscope controller 820 may be provided in a controller (control portion) 100, which will be described later.

The display 180 is a general display device, examples for which include a liquid crystal display, a CRT display, and an organic EL display. The display 180 is connected to the endoscope controller 820 to display the images processed by the image processor 822. The display 180 is also connected to the controller 100, which will be described later, to display the bend information and the like obtained by the computation apparatus 10.

The input device 190 is a general device for input, which may include a keyboard, a pointing device such as a mouse, a tag reader, buttons, a slider, and a dial. The input device 190 is connected to the controller 100. The input device 190 is employed by the user for inputting various commands to operate the computation apparatus 10. The input device 190 may be a storage medium. If this is the case, the information stored in the storage medium is input to the controller 100. The storage medium may be a memory.

The computation apparatus 10 is a device for computing bend information, which represents the bend state of the insertion portion 812, in particular, of the bendable portion 817 or the flexible tube 818 (hereinafter, these components are referred to as a flexible portion 819).

The bend information will be described with reference to FIG. 1B. In this drawing, the flexible portion 819 is illustrated by a solid line, where the flexible portion 819 has a length L that extends linearly from the point of origin $P_0$ (0, 0, 0) to the point $P_1$(0, 0, L). When the flexible portion 819 is bent as indicated in the dashed-double dotted line, the position of the point of origin $P_0$ is unchanged, but the point $P_1(0, 0, L)$ is changed to the point $P'_1(x, y, z)$. It is assumed, for the sake of convenience, that the flexible portion 819 is bent into an arc. In order to express the bend state of the flexible portion 819, two pieces of information are required, namely, the direction of the bend of the flexible portion 819 and the magnitude of this bend. The direction of the bend may be expressed as an angle θ formed by a straight line passing the point (x, y, 0) and the origin $P_0(0, 0, 0)$ with the x-axis, where the point (x, y, 0) is obtained by projecting the point $P'_1(x, y, z)$ on the xy plane. The magnitude of the bend may be represented, for example, as a curvature κ, a radius of curvature $r=\kappa^{-1}$, and a central angle $\phi=L/r=\kappa L$. The direction and magnitude of the bend that are required for the representation of the bend state of the flexible portion 819 will be referred to, throughout the specification, as bend information. As will be described later, the computation apparatus 10 computes the bend information representing the direction and magnitude of the bend at one or more detection targets 411 to be detected provided in a light guide 420 for guiding the detection light.

As shown in FIG. 1A, the computation apparatus 10 includes a sensor 500 having a sensor driver 300 and a sensor assembly 400, and the controller 100. The sensor driver 300 is provided separately from the endoscope 810, and is connected to the endoscope 810. The sensor assembly 400 is incorporated in the endoscope 810 along its longitudinal direction.

As shown in FIGS. 1A and 2, the sensor driver 300 includes a light source 310, a first light detector 320, a light branching element 330, and a generator (generate unit) 600. The sensor assembly 400 includes the light guide 420 provided with one or more detection targets 411, and a reflection member (reflector (for example, a mirror)) 430.

The light source 310 may be a light emitting unit that is commonly known, such as a lamp, an LED, a laser diode, or the like. The light source 310 may also include a florescent body or the like for the conversion of the wavelength. The light source 310 emits the light to the light guide 420, not for illumination to be supplied to the illumination optical system, but for the detection of the bend information.

The light branching element 330 is optically connected to the light source 310 and to the first light detector 320. The light branching element 330 may include an optical coupler or a beam splitter. The light branching element 330 guides the light emitted from the light source 310 to the light guide 420, and also guides the light guided by the light guide 420 to the first light detector 320.

The light guide 420 may be an optical fiber and have flexibility. A proximal end of the light guide 420 is connected to the light branching element 330. The light guide 420 is incorporated in the insertion portion 812 along its longitudinal direction, as schematically illustrated in FIG. 1A. In the light guide 420, the detection targets 411 are provided at positions in the insertion portion 812 (for example, positions in the flexible portion 819), for which the bend information should be calculated. The detection targets 411 are arranged at different positions in the longitudinal direction or circumferential direction of the flexible portion 819.

Figure 3:
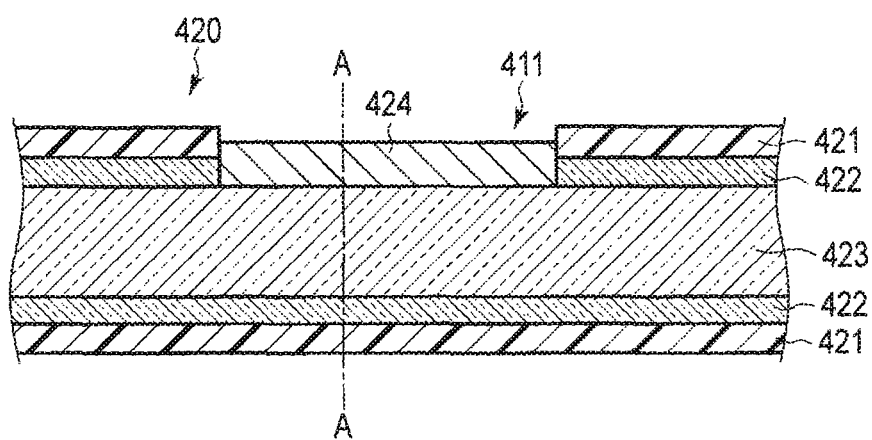
FIG. 3 is a longitudinal sectional view of a light guide.
Figure 4:
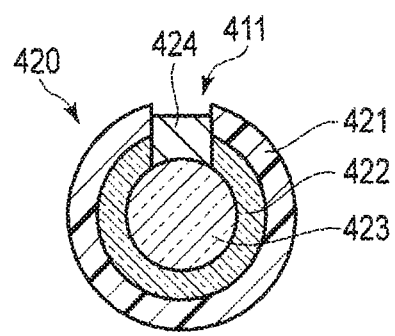
FIG. 4 is a transverse sectional view of the light guide, cut along the line A-A in FIG. 3.

FIG. 3 is a longitudinal cross-section including an optical axis of the light guide 420. FIG. 4 is a cross-section in the radial direction of the light guide 420 cut along the line A-A in FIG. 3. The light guide 420 includes a core 423, a cladding 422 surrounding the core 423, and a jacket 421 surrounding the cladding 422.

A detection target 411 is formed by removing part of the jacket 421 and the cladding 422 to expose the core 423 and providing a light absorber 424 on the exposed core 423. The light absorber 424 absorbs part of the light guided by the light guide 420. The amount of light absorbed by the light absorber 424 varies depending on the bend state of the detection target 411. The light absorbers 424 provided in the detection targets 411 have different absorption spectrum properties for different detection targets 411.

The relationship between the bend state of the detection target 411 and the transmission amount of light guided through the light guide 420 will be briefly described. When the light guide 420 is in a linear state, part of the light guided by the light guide 420 will be absorbed by the light absorbers 424. On the other hand, when the light guide 420 is bent in a manner so that the light absorbers 424 face inwardly, the amount of light striking the light absorbers 424 will decrease, thereby reducing the amount of light absorbed by the light absorbers 424. As a result, the transmission amount of light guided through the light guide 420 increases. In contrast, when the light guide 420 is bent in a manner so that the detection targets 411 face outwardly, the amount of light striking the light absorbers 424 will increase, thereby increasing the amount of light absorbed by the light absorbers 424. As a result, the transmission amount of light guided through the light guide 420 will be reduced.

In this manner, the amount of light guided by the light guide 420 varies in accordance with the bend state of the detection target 411. In other words, the detection target 411 functions as an optical modulator that modulates the light guided by the light guide 420 in accordance with the bend state of the flexible portion 819.

An optical member does not need to be limited to the light absorbers 424, and an optical member that brings some influence on the spectrum of the guided light may be employed. The optical member may be a wavelength conversion member. The detection target 411 may be formed of a substance that absorbs the light guided by the light guide 420 and emits light in a wavelength range different from that of the guided light, for example, a fluorescent material.

As shown in FIG. 2, a reflection member 430 is provided at the end of the light guide 420 that is not connected to the light branching element 330, or in other words, the distal end of the light guide 420. The reflection member 430 reflects the light guided by the light guide 420 from the light branching element 33 to return to the light branching element 330.

The first light detector 320 is a detector for detecting the light intensities for respective wavelengths. The first light detector 320 may be a spectroscope. The first light detector 320 detects a first spectrum which is the spectrum of the light guided by the light guide 420 after being reflected by the reflection member 430. The first spectrum is stored in the memory 120 via an input unit 130. The first spectrum is light amount detection information that represents the relationship between the light intensities and respective wavelengths in a predetermined wavelength range.

The light detector is not limited to a light detector having spectral properties. The light source and the light detector may include a mode in which the light amount is detected for a plurality of predetermined wavelength ranges in accordance with a combination of the light source and the light detector. For example, the light source and the light detector may include a mode in which lights of narrow bands are sequentially emitted from the light source, and the light amount in each wavelength range is detected by a broadband light detector.

The generator 600 generates suppression information for suppressing the first change information in the second change information. The generation of the suppression information will be described later.

The first change information represents, for example, a change in the spectrum that is not derived from the bend of the detection target 411. Examples of changes in the spectrum that are not derived from the bend of the detection targets 411 may include a change in the spectrum of the light source 310. The spectrum of the light source 310 (hereinafter referred to as the second spectrum) is, for example, the spectrum of the light that is immediately after the emission from the light source 310, and is the spectrum of the light guided to the generator 600 by the light guide 601 that is different from the light guide 420. In other words, the light guided to the generator 600 by the light guide 601 is not modulated by the detection targets 411. The second spectrum is light amount detection information that represents the relationship between the light intensities and respective wavelengths in a predetermined wavelength range.

The second change information includes the first change information, and represents a change in the spectrum derived from the bend of the detection targets 411. The second change information is calculated by a bend information arithmetic operator 110, which will be described later, based on the first spectrum stored in the memory 120.

According to the present embodiment, a change in the spectrum derived only from the bend of the detection targets 411 is referred to as third change information, as will be described later. That is, the third change information is obtained by removing the first change information from the second change information. In other words, the second change information includes the third change information that is derived only from the bend, and the first change information that is not derived from the bend and that is superimposed on the third change information.

In the generator 600, the second spectrum has already been known. The generator 600 includes a light guide 601, a second light detector 603, and a generator main body (hereinafter referred to as a main body 605).

The light guide 601 is a member arranged separately from the light guide 420. The light guide 601 is optically connected to the light source 310 at one end thereof, and optically connected to the second light detector 603 at the other end thereof. The light guide 601 guides the detection light emitted from the light source 310 to the second light detector 603 so as not to pass through any of the detection targets 411 or the like. The light guide 601 may be an optical fiber and have flexibility.

The second light detector 603 detects the light intensities for respective wavelengths. The second light detector 603 detects, for example, a spectrum of light that is not modulated by any of the detection targets 411, or in other words, the second spectrum. The second light detector 603 may be a spectroscope. The second light detector 603 outputs the second spectrum to the main body 605.

The main body 605 generates the first change information based on the second spectrum. The second light detector 603 may output the second spectrum to the bend information arithmetic operator 110 so that the bend information arithmetic operator 110 can generate the first change information. Alternatively, the second spectrum may be stored in the memory 120 so that the main body 605 or the bend information arithmetic operator 110 can generate the first change information based on the second spectrum stored in the memory 120. When the first change information is generated by the bend information arithmetic operator 110, the first change information may be output to the main body 605, or may be stored in the memory 120 and read out in the main body 605.

The main body 605 generates the suppression information based on the first change information, and outputs it to the controller 100. The generation of the suppression information will be described later. The main body 605 may be arranged in the controller 100, or the main body 605 may be included in the bend information arithmetic operator 110.

Next, the controller 100 of the computation apparatus 10 will be described by referring to FIG. 1A. The controller 100 can be constituted by an electronic computer such as a personal computer. The controller 100 includes an arithmetic operator (arithmetic operation portion) 101, an endoscope bend information calculator (endoscope bend information calculation portion) 140, a light detector driver (light detector drive portion) 150, and an output unit 160.

The arithmetic operator 101 includes the input unit 130, the memory 120, and the bend information arithmetic operator 110.

The first spectrum is input from the first light detector 320 to the input unit 130, and the suppression information is input from the main body 605 to the input unit 130. The input unit 130 transmits the input first spectrum and the suppression information to the bend information arithmetic operator 110. The light amount information relationship of the detection targets 411, which will be described later, may also be input from the input device 190 to the input unit 130. In addition, the information output from the endoscope controller 820 is also input to the input unit 130. The input unit 130 transmits the information that has been input in such a manner, to the bend information arithmetic operator 110 or to the light detector driver 150.

The memory 120 stores various types of information that is required for the operation performed by the bend information arithmetic operator 110. The memory 120 stores, for example, programs including calculation algorithms and the relationship of light amount information of the detection targets 411.

The light amount information relationship indicates, for example, the relationship between the absorption spectrum of the light absorber 424 disposed in each of the detection targets 411, the intensity of the light modulated by the detection targets 411, and the bend information.

The bend information arithmetic operator 110 calculates the bend information of a detection target 411, based on the second change information, the suppression information, and the light amount information relationship stored in the memory 120. The bend information arithmetic operator 110 includes a first arithmetic operator 212 and a second arithmetic operator 214. Based on the second change information, the suppression information, and the light amount information relationship stored in the memory 120, the first arithmetic operator 212 calculates the light amount change information for each detection target 411. The second arithmetic operator 214 calculates the bend information at the detection target 411, based on the light amount change information calculated by the first arithmetic operator 212 and the curvature coefficient stored in the memory 120. The bend information arithmetic operator 110 transmits the calculated bend information to the endoscope bend information calculator 140. The bend information arithmetic operator 110 further outputs the information on the operations of the first light detector 320 and the second light detector 603 to the light detector driver 150.

Based on the bend information of the detection targets 411 calculated by the bend information arithmetic operator 110, the endoscope bend information calculator 140 calculates the bend information of the insertion portion 812 in which the detection targets 411 are arranged. The calculated bend information is transmitted to the output unit 160. The endoscope bend information calculator 140 may be incorporated in the bend information arithmetic operator 110.

The light detector driver 150 generates drive signals for the first light detector 320 and the second light detector 603, based on the information acquired from the input unit 130 and the bend information arithmetic operator 110. In response to these drive signals, the light detector driver 150 turns the first light detector 320 and the second light detector 603 on/off for their operations, for example, in accordance with the user's instructions acquired via the input unit 130. In response to the drive signals, the light detector driver 150 may also adjust the gains of the first light detector 320 and the second light detector 603, based on the information acquired from the bend information arithmetic operator 110. The light detector driver 150 may be further configured to generate a drive signal for controlling the operation of the light source 310. The light detector driver 150 transmits the generated drive signals to the output unit 160.

The output unit 160 outputs to the display 180 the bend information of the detection targets 411 acquired from the bend information arithmetic operator 110 and the bend information of the insertion portion 812 acquired from the endoscope bend information calculator 140. The output unit 160 outputs the acquired bend information to the endoscope controller 820. The output unit 160 outputs the drive signals acquired from the light detector driver 150, to the light source 310, the first light detector 320, and the second light detector 603.

The endoscope controller 820, the main body 605, the input unit 130, the bend information arithmetic operator 110, the endoscope bend information calculator 140, the light detector driver 150, and the output unit 160 may be implemented by a hardware circuit including, for example, an ASIC. At least one of the endoscope controller 820, the main body 605, the input unit 130, the bend information arithmetic operator 110, the endoscope bend information calculator 140, the light detector driver 150, and the output unit 160 may be implemented by a processor including, for example, a CPU. In case at least one of these components is implemented by a processor, an internal memory or an external memory, which are not shown in the drawings, may be arranged in a manner so as to be accessible from the processor. The internal memory or the external memory stores program codes for causing the processor to function as at least one of these components by executing the codes by the processor. The endoscope controller 820, the main body 605, the input unit 130, the bend information arithmetic operator 110, the endoscope bend information calculator 140, the light detector driver 150, and the output unit 160 may be configured as a single processor or as a plurality of processors. In the latter case, the processing may be performed in a coordinated manner by transmitting and receiving data to and from each other. In addition, in the latter case, the processors may also be arranged in different casings.

Next, the operations of the endoscope system 1 and the computation apparatus 10 according to the present embodiment will be described.

The insertion portion 812 of the endoscope 810 is inserted into the insertion target by the user. During this insertion, the insertion portion 812 is bent in accordance with the internal shape of the insertion target. The endoscope 810 acquires an image signal from the observation optical system and the imaging sensor in the insertion portion 812. The acquired image signal is transmitted to the image processor 822 of the endoscope controller 820. Based on the acquired image signal, the image processor 822 creates an image of the inside of the insertion target. The image processor 822 causes the display 180 to present the created image.

If the user desires to display the bend information of the insertion portion 812 on the display 180, or to have the endoscope controller 820 implement various operations using the bend information of the insertion portion 812, the user inputs to this effect to the controller 100 on the input device 190. In response, the operation of the computation apparatus 10 is initiated.

When the computation apparatus 10 starts operating, the light source 310 of the sensor driver 300 emits light within a predetermined emission wavelength range. The light emitted from the light source 310 is guided to the light guide 420 of the sensor assembly 400 via the light branching element 330. The guided light is transmitted through the light guide 420 from its proximal side to the distal side. At this point, the amount of light in the light guide 420 changes in accordance with the bend state of the detection targets 411 provided in the light guide 420, and the amount of light transmitted changes for each wavelength. This light is then reflected by the reflection member 430 to return through the light guide 420 from its distal side to the proximal side. In the reflected light, the amount of light changes again at the detection targets 411, and the amount of light transmitted changes for each wavelength. In other words, the reflected light is again affected by the change in the amount of light at the detection targets 411. The reflected light reaches the first light detector 320 via the light branching element 330. The first light detector 320 detects the intensities of the received light, for different wavelengths.

The first light detector 320 detects the first spectrum representing the intensities of the light for different wavelengths. The bend information arithmetic operator 110 generates the second change information based on the first spectrum.

The light emitted from the light source 310 is also detected by the second light detector 603 via the light guide 601.

The operations of the first light detector 320, the generator 600, and the bend information arithmetic operator 110 are now described.

In the following description, at time T0, the detection targets 411 are in the reference state which may be a linear state.

The first spectra I0 and I1 at times T0 and T1, respectively, are discussed first. Time T1 is the time that is a predetermined period of time after time T0.

At time T1, the detection targets 411 are in a state that has been changed from the reference state, for example, into a bend state.

Figure 5:
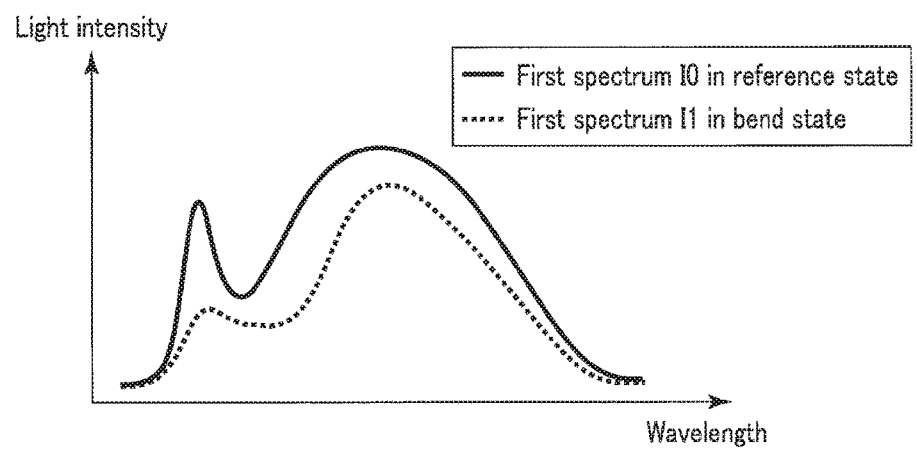
FIG. 5 is a diagram showing, regarding the first spectrum representing the relationship between the light intensities and wavelengths in a predetermined wavelength range, the relationship between the first spectrum I0 in a reference state and the first spectrum I1 in the bend state.

FIG. 5 shows the relationship between the first spectra I0 and I1, which is the relationship between the light intensities and wavelengths in the predetermined wavelength range, and which is detected by the first light detector 320 at times T0 and T1. The first spectrum I0 at time T0 indicates the spectrum of a detection target 411 in the reference state. The first spectrum I1 at time T1 indicates the spectrum of the detection target 411 in the bend state. When the detection target 411 is bent, the amount of light absorbed by the light absorber 424 changes depending on the direction and magnitude of the bend. It is assumed here that the change of the spectrum of the light source 310 (first change information) is not considered.

Next, the change rate of the first spectra I0 and I1 is now described.

Figure 6:
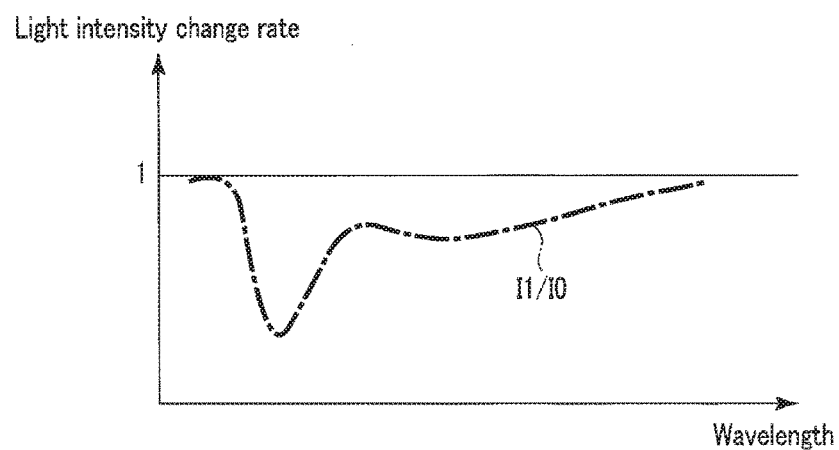
FIG. 6 is a diagram showing the change rate of the light intensities at respective wavelengths, specifically the bend change rate of the first spectrum I1 in the bend state with respect to the first spectrum I0 in the reference state.

FIG. 6 shows the change rate (I1/I0) in light intensities at respective wavelengths, specifically, the change rate of the first spectrum I1 in the bend state with respect to the first spectrum I0 in the reference state. This change rate will be referred to as the bend change rate. The bend change rate is the change rate of the spectrum derived only from the bend of the detection targets 411, and it is referred to as the third change information.

The second spectra Q0 and Q2 at times T0 and T2 are described. Time T2 is a time that is a predetermined period of time after time T0, and is different from time T1.

At time T2, the detection targets 411 remain in the reference state, whereas the spectrum of the light source 310 has been changed.

Figure 7:
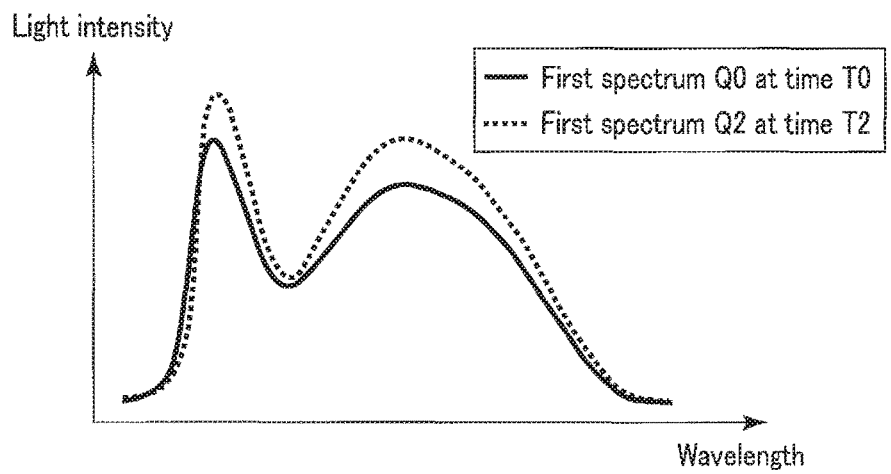
FIG. 7 is a diagram showing, regarding the second spectrum showing the relationship between the light intensities and wavelengths in a predetermined wavelength range, the relationship between the second spectrum Q0 at time T0 and the second spectrum Q2 at time T2.

FIG. 7 shows the relationship between the second spectra Q0 and Q2, which represents the relationship between the light intensities and wavelengths in a predetermined wavelength range, and which is detected by the second light detector 603 at times T0 and T2. The second spectrum Q0 indicates the second spectrum at time T0. The second spectrum Q2 indicates the second spectrum at time T2, which is a predetermined period of time after time T0. The second spectrum Q2 changes with respect to the second spectrum Q0 as a predetermined period of time elapses, due to at least one of the ambient temperature around the light source 310, the drive current of the light source 310, the heat generated by the light emitting elements of the light source 310, and change of the light source 310 over time. The second spectra Q0 and Q2 are detected by the second light detector 603, and become known data.

The second spectra Q0 and Q2 are not affected by the bend state of the detection targets 411.

Next, the change rate of the second spectra Q0 and Q2 will be discussed.

Figure 8:
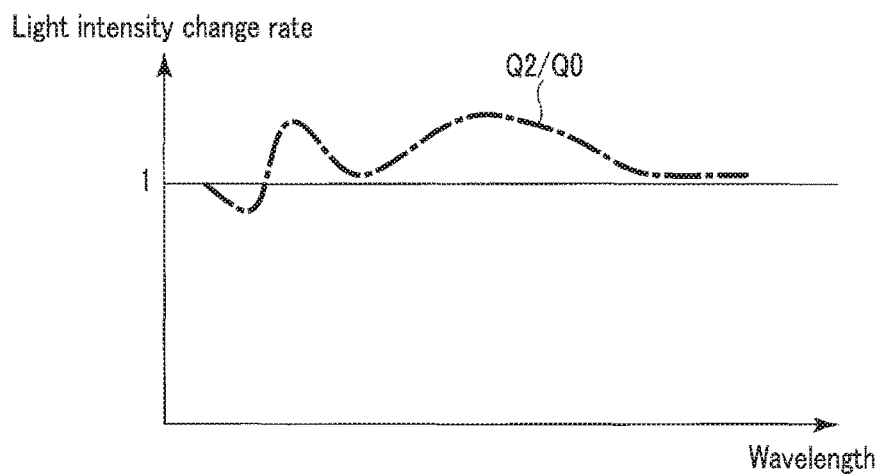
FIG. 8 is a diagram showing the change rate of the light intensities at respective wavelengths, specifically, the light source change rate of the second spectrum Q2 at time T2 with respect to the second spectrum Q0 at time T0.

FIG. 8 shows the change rate in light intensities at respective wavelengths, specifically the change rate (Q2/Q0) of the second spectrum Q2 at time T2 with respect to the second spectrum Q0 at time T0. This change rate will be hereinafter referred to as a light source change rate. The light source change rate is the change rate of the spectrum of the light source 310, and is referred to as the first change information. This light source change rate may be calculated by the main body 605 of the generator 600, and, after the calculation, it may be output to the bend information arithmetic operator 110 via the input unit 130. The light source change rate (Q2/Q0) is already known because it is based on the known Q2 and Q0.

Now, at time T3, which is a predetermined period of time after time T0, the first spectrum I3 of the light detected by the first light detector 320 and the bend change rate (third change information) of the light will be considered. At time T3, in a manner similar to time T2, the spectrum of the light source 310 changes from the second spectrum Q0 to the second spectrum Q2, and the detection targets 411 remain in the reference state.

At time T0, the detection targets 411 are in the reference state. In such a state, when the light having the first spectrum I0 is guided through the light guide 420, the first spectrum I0 is detected by the first light detector 320. When the light having the second spectrum Q0 is guided through the light guide 601, the second spectrum Q0 is detected by the second light detector 603.

At time T3, which is a predetermined period of time after time T0, the detection targets 411 remain in the reference state in a manner similar to time T0. The light having the spectrum Q2 is guided to the light guide 601 due to a change in the spectrum of the light source 310. At time T3, in a manner similar to the case of time T2, the spectrum Q2 is detected by the second light detector 603. Since the detection targets 411 are in the reference state at time T3, no change of the spectrum that is derived only from bending (i.e., the third change information) will be incurred. This means that, at time T3, only a change of the spectrum that is not derived from the bending (i.e., the first change information) occurs. With the detection targets 411 that are in the reference state, the spectrum detected by the first light detector 320 will be the first spectrum I3, which is supposed to be the same as the first spectrum I0 obtained at time T0, as illustrated in FIG. 5. However, the second spectra Q0 and Q2 obtained at times T0 and T3 need to be taken into consideration for the first spectrum I3 detected at time T3 by the first light detector 320. Thus, the first spectrum I3 is expressed as I0×Q2/Q0. As discussed above, even if the shapes of the detection targets 411 remain unchanged, a change may be caused in the spectrum of the light source 310, as a result of which the first change information (light source change rate) that is not derived from the bending may be superimposed onto the first spectrum.

The bend change rate of the first spectrum I3 at time T3 (reference state) with respect to the first spectrum I0 at time T0 (reference state) is I3/I0=Q2/Q0, which is calculated by the bend information arithmetic operator 110.

Next, at time T4, which is a predetermined period of time after time T0, the first spectrum I4 of the light detected by the first light detector 320 and the bend change rate (third change information) of the light will be considered. At time T4, the spectrum of the light source 310 changes from the second spectrum Q0 to the second spectrum Q2 in a manner similar to time T2, and the detection targets 411 are changed from the reference state to the bend state in a manner similar to time T1.

At time T0, the detection targets 411 are in the reference state. When the light having the first spectrum I0 is guided through the light guide 420, the first light detector 320 detects the first spectrum I0. When the light of the second spectrum Q0 is guided through the light guide 601, the second light detector 603 detects the second spectrum Q0.

Figure 9:
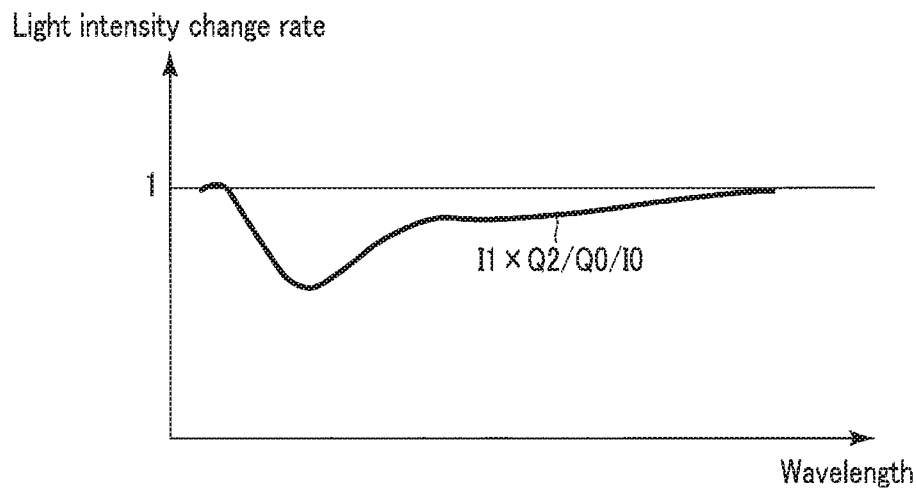
FIG. 9 is a diagram showing the change rate in light intensities at respective wavelengths, specifically, the change rate of the first spectrum I4 in the bend state at time T4 with respect to the first spectrum I0 in the reference state at time T0.

At time T4, which is a predetermined period of time after time T0, the detection targets 411 are in a bend state that is different from time T0. Under such conditions, when the light having the second spectrum Q2 is guided through the light guide 601, the second light detector 603 detects the second spectrum Q2. With the detection targets 411 in a bend state, the spectrum detected by the first light detector 320 will be the first spectrum I4, which is supposed to be the same as the first spectrum I1 obtained at time T1 as shown in FIG. 5. However, for the first spectrum I4 detected at time T4 by the first light detector 320, the second spectra Q0 and Q2 obtained at times T0 and T4 need to be taken into consideration. Thus, the first spectrum I4 is expressed as I1×Q2/Q0. As indicated in FIG. 9, the bend change rate of the first spectrum I4 at time T4 (bend state) with respect to the first spectrum I0 at time T0 (reference state) is expressed as I4/I0=I1×Q2/Q0/I0. This change rate is the second change information that includes the first change information (Q2/Q0), which is calculated by the bend information arithmetic operator 110. Because of the first change information included in the second change information, the bend information calculated on the basis of the second change information is not the same as the actual bend information. In other words, there is a difference between the bend information calculated on the basis of the second change information and the actual bend information because of the first change information, and therefore accurate bend information may not be obtained. Thus, the first change information should be suppressed so that the bend information can be calculated on the basis of only the third information shown in FIG. 6.

Figure 10:
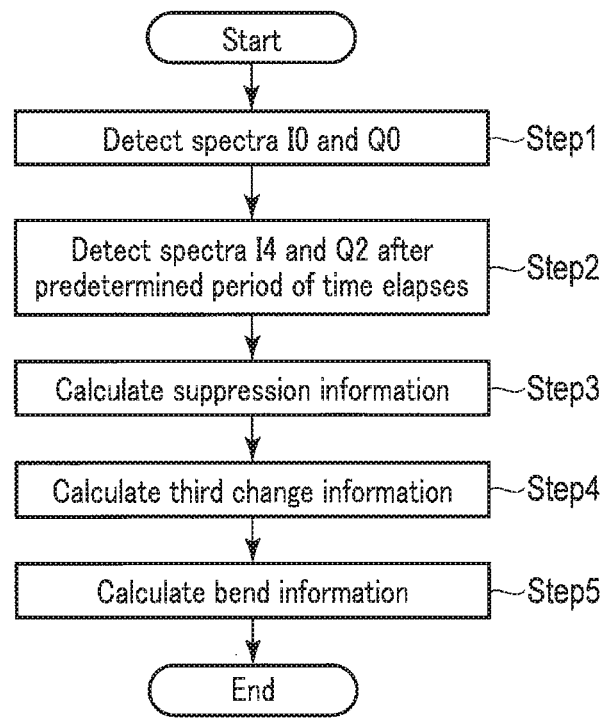
FIG. 10 is a flowchart showing part of the flow of processing at a controller.

The procedure for calculating the third change information while suppressing the first change information will be described by referring to FIG. 10. When the detection targets 411 are in the reference state at time T0, the first light detector 320 detects the first spectrum I0, and the second light detector 603 of the generator 600 detects the second spectrum Q0 (Step 1).

At time T4, which is a predetermined period of time after time T0, when the detection target 411 is in the bend state, the first light detector 320 detects the first spectrum I4, and the second light detector 603 of the generator 600 detects the second spectrum Q2 (Step 2).

With the second spectra Q0 and Q2 at times T0 and T4 taken into consideration, the first spectrum I4 is expressed as I1×Q2/Q0. The bend change rate of the first spectrum I4 at time T4 (bend state) with respect to the first spectrum I0 at time T0 (reference state) is expressed as I4/I0=I1×Q2/Q0/I0.

In order to suppress the first change information, the main body 605 of the generator 600 operates the reciprocal of the light source change rate (Q2/Q0), which is the first change information, as the suppression information that can suppress the first change information in the second change information (Step 3). That is, the main body 605 operates the reciprocal Q0/Q2 as the suppression information. Q0/Q2 is calculated based on the detection results of the second light detector 603. Because the known Q2 and Q0 are used, Q0/Q2 is also known. The main body 605 outputs the suppression information to the bend information arithmetic operator 110 via the input unit 130.

The bend information arithmetic operator 110 calculates the third change information based on the second change information (I4/I0) and the suppression information (Q0/Q2) (Step 4). That is, the bend information arithmetic operator 110 extracts the third change information from the second change information. For this purpose, the bend information arithmetic operator 110 performs the calculation of the following expression (1):

$$(I4/I0) \times (Q0/Q2) = (I1 \times Q2/Q0/I0) \times (Q0/Q2) \quad \text{(Expression 1)}$$
$$= I1/I0$$

In this manner, the bend information arithmetic operator 110 calculates the third change information (I1/I0) by removing the first change information (Q2/Q0) from the second change information (I4/I0) using the suppression information (Q0/Q2).

The bend information arithmetic operator 110 calculates the bend information (direction and magnitude of the bend) of the detection targets 411 based on the third change information (Step 5).

The calculated bend information of the detection targets 411 is acquired by the endoscope bend information calculator 140. The endoscope bend information calculator 140 calculates the bend information of the insertion portion 812 based on the acquired bend information.

The bend information of the detection targets 411 calculated by the bend information arithmetic operator 110 and the bend information of the insertion portion 812 calculated by the endoscope bend information calculator 140 are acquired by the endoscope controller 820 via the output unit 160. Furthermore, the bend information is displayed on the display 180 via the output unit 160.

Moreover, the information input to the input unit 130 and the bend information of the detection targets 411 calculated by the bend information arithmetic operator 110 are acquired by the light detector driver 150. Based on the acquired information, the light detector driver 150 transmits the drive signals to the first light detector 320 and the second light detector 603 via the output unit 160 to control the operations of the first light detector 320 and the second light detector 603.

As described above, according to the present embodiment, even if the second change information includes the first change information, the third change information representing the change of the spectrum derived only from the bend of the detection targets 411 can be calculated based on the suppression information. Thus, even if there is a difference between the calculated bend information and the actual bend information, this difference can be eliminated from the third change information, and the accurate bend information can be obtained. This difference relates to a change in the spectrum that is not derived from the bend of the detection targets 411. In addition, based on this acquired bend information, the bend information of the insertion portion 812 can be calculated by the endoscope bend information calculator 140. As a result, the user can be aware of the bend information of the detection targets 411 and the insertion portion 812 during the operation of the endoscope 810.

According to the present embodiment, the first light detector 320 and the second light detector 603 are separately provided so that the light detectors can individually focus on their own detection operations. In addition, in the event of a problem in detection, only a light detector having the problem can be replaced with a new light detector, while a light detector having no problem can continue to be used.

The second light detector 603 detects the second spectrum Q0, for example, during a calibration. This calibration is performed, for example, when the detection targets 411 are in a reference state such as a linear state, and the operations that the detection targets 411 carry out have reached a predetermined number. The calibration may be performed every time the endoscope 810 is connected to the computation apparatus 10, or may be performed at any desired timing.

The second light detector 603 detects the second spectrum Q2 at, for example, any of the following timings 1 to 5.

At timing 1, the second light detector 603 may detect the second spectrum Q2 every time the first light detector 320 detects the first spectrum I1. That is, the detection timing of the second light detector 603 corresponds to the detection timing of the first light detector 320.

At timing 2, when the first light detector 320 detects the first spectrum I1 for a predetermined number of times, the second light detector 603 detects the second spectrum Q2. That is, the number of detections of the second light detector 603 is smaller than the number of detections of the first light detector 320. For example, for every ten times the first light detector 320 performs the detections, the second light detector 603 may perform one detection.

At timing 3, the second light detector 603 detects the second spectrum Q2 at predetermined time intervals. That is, the second light detector 603 independently performs detections, regardless of the detection of the first light detector 320. For example, the second light detector 603 may perform a detection every second.

At timing 4, when the temperature of the light source 310 changes beyond a predetermined range, the second light detector 603 may detect the second spectrum Q2. When the temperature of the light source 310 changes by ±0.2° C. or more with respect to a desired value, the second light detector 603 detects the second spectrum Q2. In such a configuration, a temperature sensor will be required for measurement of the temperature of the light source 310.

At timing 5, when the brightness of the light source 310 changes in accordance with the drive current that flows into the light source 310, the second light detector 603 detects the second spectrum Q2.

As described above, the second light detector 603 detects the second spectra Q0 and Q2 when the operations that the detection targets 411 carry out in the reference state have reached a predetermined number, when a predetermined period of time has elapsed, when a predetermined amount of change occurs in the temperature of the light source 310, or when the operation state of the light source 310 is changed.

In relation to the first change information, it is assumed that the light source 310 is known in advance as having a light intensity that changes while the ratio of the wavelength to the respective light intensity is kept constant. That is, the light source change rate (Q2/Q0) would not depend on the wavelength. In such a configuration, the second light detector 603 may be a light intensity sensor that is not designed to detect the light intensity with respect to the wavelength.

When the difference between the second spectrum Q0 and the second spectrum Q2 is small and the light source change rate (Q2/Q0) is close to 1, the main body 605 determines the suppression information as 1 so that the load of the bend information arithmetic operator 110 can be reduced.

If the wavelength range in which the first change information is pronounced is known in advance, the main body 605 may generate the suppression information only for this specific wavelength range so that the load of the bend information arithmetic operator 110 can be reduced.

Although the bend of the insertion portion 812 has been discussed as an example target of the computation at the bend information arithmetic operator 110, the target is not limited thereto. A distortion may be the target for detection in health monitoring of a structure.

The first light detector 320 and the second light detector 603 may be formed of an element such as a color filter that transmits only a predetermined wavelength range, and a light receiving element such as a photodiode.

Although not shown in the drawings, the first light detector 320 and the second light detector 603 may be multichannel light detectors that respectively detect the spectra of light incident from different ports. If this is the case, the light detector may be formed as one unit that can detect the spectra from multiple ports.

The second light detector 603 may be configured to detect the light diffused from the light guide 420, instead of detecting light directly from the light source 310.

First Modification

The first modified example of the present embodiment will be described below with reference to FIG. 11.

As shown in FIG. 11, the generator 600 may be provided with a beam splitter 607 to split the light emitted from the light source 310 into the light travelling to the light branching element 330 and the light travelling to the second light detector 603. The beam splitter 607 is disposed between the light source 310 and the light branching element 330 in the light traveling direction. The light guide 601 may be omitted if the light directly enters the second light detector 603 from the beam splitter 607, or may be disposed between the beam splitter 607 and the second light detector 603.

Second Modification

The second modification of the present embodiment will be described below with reference to FIG. 12.

As shown in FIG. 12, the generator 600 is provided with a light branching element 330. The light branching element 330 according to the present embodiment guides part of the light emitted from the light source 310 to the light guide 420 so that the light guided by the light guide 420 can be guided to the first light detector 320, while guiding the remaining part of the light emitted from the light source 310, to the second light detector 603.

Second Embodiment

The second embodiment will be described with reference to FIGS. 13A, 13B, 13C, and 13D. According to this embodiment, only portions different from the first embodiment will be described.

According to the present embodiment, the second light detector 603 is omitted, and the generator 600 is provided with a light guide 601, a switch 609, a first light detector 320, and a main body 605.

The light guide 601 is optically connected to the light source 310 at one end thereof, and also optically connected to the switch 609 at the other end thereof. The light guided to the switch 609 by the light guide 601 is the light that is emitted from the light source 310 and is not modulated by the detection targets 411.

The switch 609 is disposed between the light guide 601 and the first light detector 320 and between the light branching element 330 and the first light detector 320 in the light traveling direction.

Figure 13A:
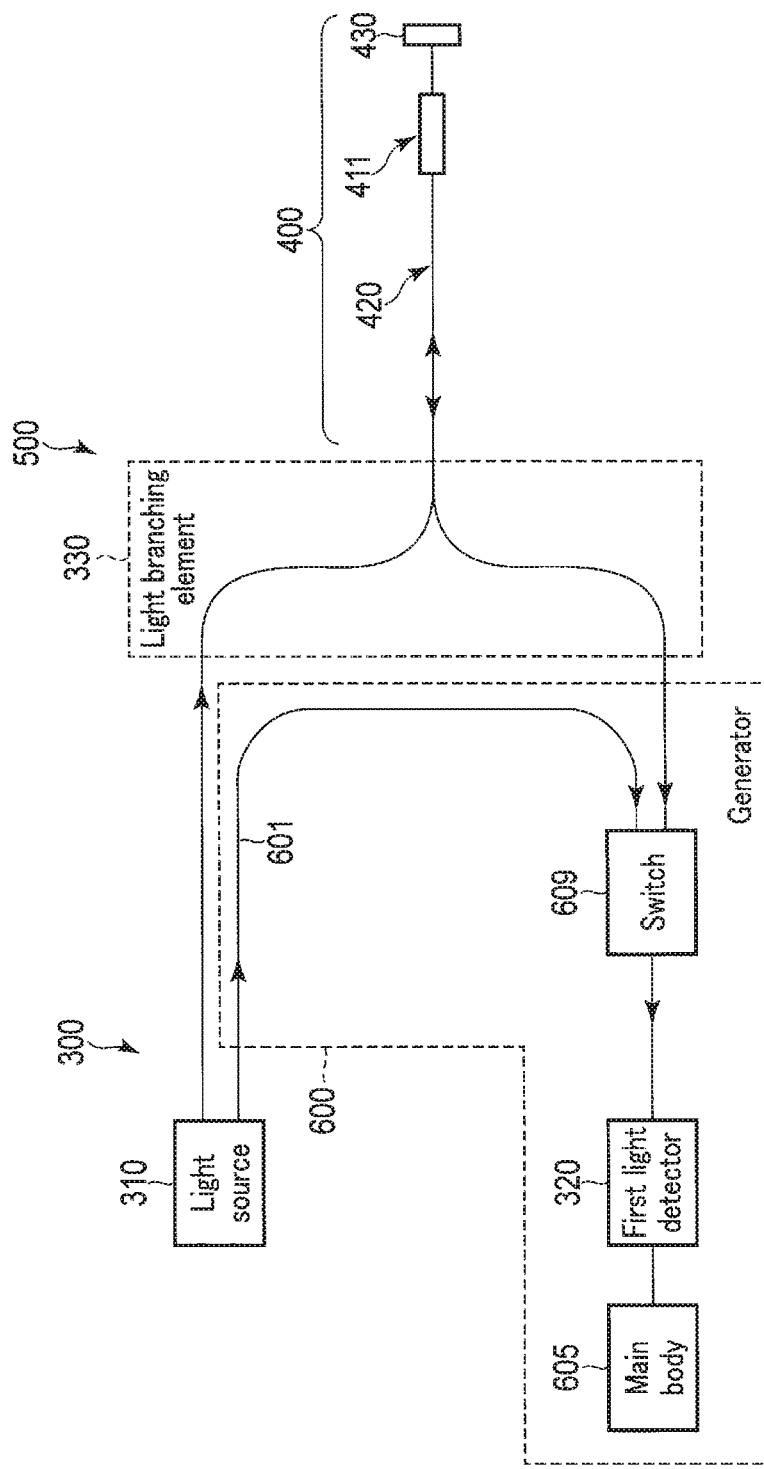
FIG. 13A is a block diagram showing an example configuration of a sensor according to the second embodiment.
Figure 13B:
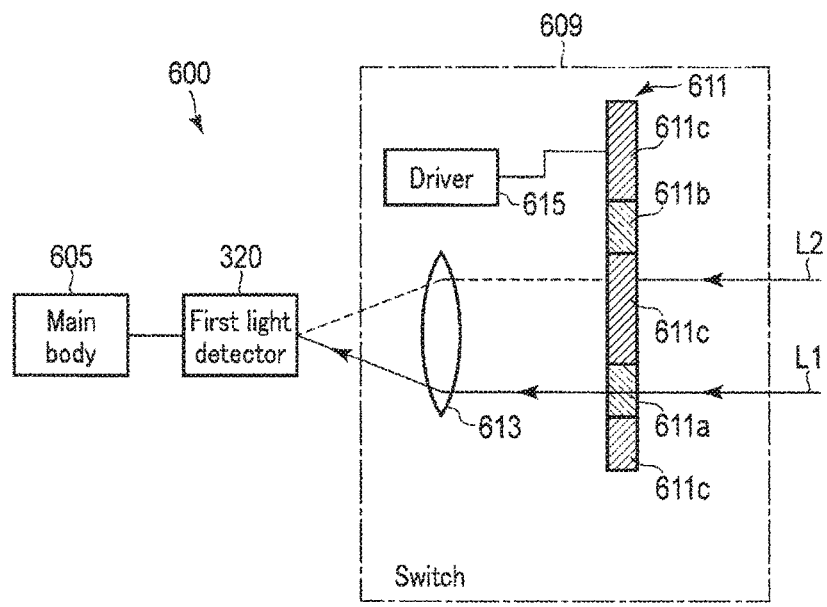
FIG. 13B is a diagram showing a switching member in the first state.
Figure 13C:
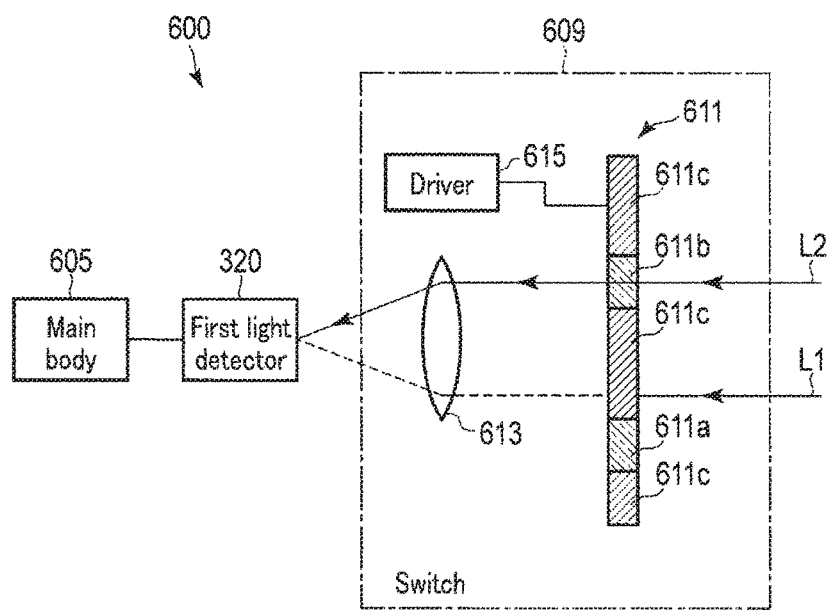
FIG. 13C is a diagram showing the switching member of FIG. 13B in the second state.
Figure 13D:
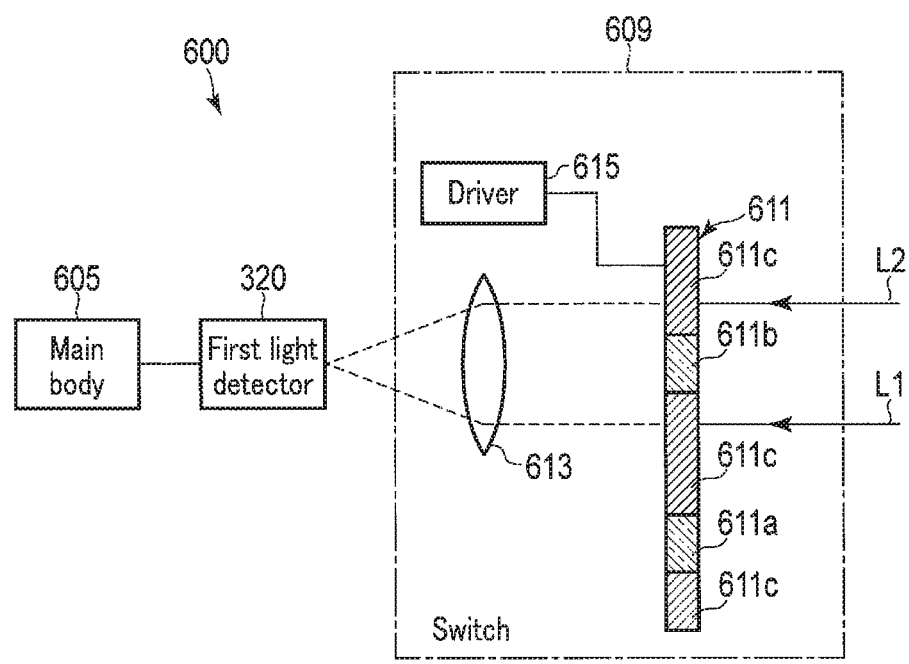
FIG. 13D is a diagram showing the switching member of FIG. 13B in the third state.

Here, the light transmitted from the light branching element 330 to the switch 609 through the light guide 420 is referred to as the first light L1, and the light transmitted from the light source 310 directly to the switch 609 through the light guide 601 is referred to as the second light L2. As shown in FIGS. 13B and 13C, the switch 609 shields either the first light L1 or the second light L2. Thus, the light detected by the first light detector 320 is either the first light L1 or the second light L2. As shown in FIG. 13D, the switch 609 may also shield both the first light L1 and the second light L2 in the switching. In this manner, the switch 609 switches the spectrum that is to be detected by the first light detector 320, between the first spectrum of the first light L1 and the second spectrum of the second light L2. Based on the first change information on the second spectrum detected by the first light detector 320, the main body 605 generates the suppression information.

The switch 609 is provided with a switching member 611, an optical member 613 such as a lens disposed between the switching member 611 and the first light detector 320, and a driver 615 that drives the switching member 611.

The switching member 611 may be a plate member. The switching member 611 includes a first transmission portion 611a through which the first light L1 is transmitted, a second transmission portion 611b through which the second light L2 is transmitted, and a light shield portion 611c that selectively shields the first light L1 and the second light L2.

In general, the amount of first light L1 is smaller than the amount of second light L2. This is attributed to the loss of the first light L1 at the light branching element 330, the detection targets 411, and the reflection member 430. When the first light detector 320 respectively receives the first light L1 and the second light L2 and their light amounts are equal, the driving conditions of the first light detector 320 will be the same for both lights. For this reason, it is preferable that the light transmittance of the second transmission portion 611b be set lower than the light transmittance of the first transmission portion 611a so that the amounts of light received by the first light detector 320 will become equal.

When the light source 310 is an excitation-type white LED, the wavelength component of the excitation light has a high intensity. In addition, the light intensity of a specific wavelength in the excitation light emitted from the light source 310 may need to be increased in accordance with the absorption spectrum of the light absorber 424. For such a case, in order to use the first light detector 320 with its dynamic range in appropriate conditions, it is preferable that the transmission spectrum of the second transmission portion 611b be determined so as to attenuate specific wavelengths. For this purpose, the transmission spectrum of the second transmission portion 611b should be differentiated from the transmission spectrum of the first transmission portion 611a.

As discussed above, the light transmittance of the second transmission portion 611b is lower than the light transmittance of the first transmission portion 611a, and/or the transmission spectrum of the second transmission portion 611b is different from the transmission spectrum of the first transmission portion 611a.

The first transmission portion 611a and the second transmission portion 611b may be provided with, for example, an optical member such as a lens disposed in a through hole of the plate member. If there is no need to consider the light transmittance and the transmission spectrum, through holes may be arranged in place of the first transmission portion 611a and the second transmission portion 611b.

The light shield portion 611c is a region other than the first transmission portion 611a and the second transmission portion 611b in the switching member 611, and is provided with a light shielding cover. The material of the light shield portion 611c may be a metal such as copper or stainless steel. The light shield portion 611c may be configured to diffuse, absorb, or reflect the light.

The optical member 613 guides the light transmitted through the switching member 611 to the first light detector 320.

The driver 615 switches the switching member 611 to one of the first to third states, which will be described later. The driver 615 therefore may be configured to move the switching member 611. This move is carried out in a direction between the top and bottom of the drawing sheets of FIGS. 13B, 13C, and 13D, but the invention is not limited to this direction, and may be realized by rotation.

As shown in FIG. 13B, the driver 615 switches the switching member 611 to the first state. Then, the first light L1 is transmitted through the first transmission portion 611a to be guided to the first light detector 320 by the optical member 613, and is detected by the first light detector 320. On the other hand, the second light L2 is shielded by the light shield portion 611c, and therefore will not be detected by the first light detector 320. As a result, the first light detector 320 functions in a manner similar to the first light detector 320 of the first embodiment. This means that the first light detector 320 detects the first spectrum. Furthermore, the main body 605 may be configured to generate the second change information based on the first spectrum.

As illustrated in FIG. 13C, the driver 615 switches the switching member 611 to the second state. The second light L2 is therefore transmitted through the second transmission portion 611b to be guided to the first light detector 320 by the optical member 613, and is detected by the first light detector 320. The first light L1 is shielded by the light shield portion 611c, and will not be detected by the first light detector 320. As a result, the first light detector 320 functions in a manner similar to the second light detector 603 of the first embodiment. This means that the first light detector 320 detects the second spectrum. The main body 605 generates the suppression information.

The switching member 611 may be switched to the second state by the driver 615 at the same timings as the timings 1 to 5 discussed in the first embodiment. In addition, when the operations that the detection targets 411 carry out in the reference state have reached a predetermined number, when a predetermined period of time has elapsed, when a predetermined amount of change occurs in the temperature of the light source 310, or when the operation state of the light source 310 is changed, the switching member 611 may be switched to the second state by the driver 615. Here, the first light detector 320 may detect the second spectrum by switching at the switch 609.

According to the present embodiment, the same effect as that of the first embodiment can be achieved. Furthermore, according to the present embodiment, the first light detector 320 is used for the detection of both the first light L1 and the second light L2. That is, the first change information and the second change information are output in a switching manner by a single light detector, for example in accordance with time. This can eliminate the possibility of the light detectors causing any difference in characteristics, improve the effect of suppressing the first change information, reduce the number of light detectors required, and also reduce costs.

As shown in FIG. 13D, the driver 615 switches the switching member 611 to the third state, in response to which the light shield portion 611c shields the first light L1 and the second light L2 so that the first light L1 and the second light L2 are not detected by the first light detector 320. The light shield portion 611c can shield both the first light L1 and the second light L2 at the same time.

In the above manner, the first light detector 320 acquires a dark current (dark-time output). In accordance with a change in the surrounding environment of the first light detector 320, the temperature of the first light detector 320 also changes. This also changes the output of the first light detector 320. The change in the output can be suppressed by acquiring the dark-time output of the first light detector 320.

According to the present embodiment, the dark-time output of the first light detector 320 can be measured without turning off the light source 310. Once the light source 310 is turned off, heat will no longer be generated by the light source 310, which causes a temperature change in the light source 310. This tends to increase the change in the spectrum of the light source 310 when the light source 310 is turned on again. In order to avoid this, the temperature change in the first light detector 320 can be suppressed, and a change in the spectrum of the light source 310 can be suppressed.

The driver 615 carries out the switching based on the transition between the first state and the second state. This is because a change in the output caused by a temperature change in the first light detector 320 is smaller than a change in the spectrum of the light source 310.

When the detection targets 411 are in the reference state and the first light detector 320 detects the first spectrum I0 and the second spectrum Q0, it is preferable that the driver 615 switch the switching member 611 to the third state so that the first light detector 320 can acquire the dark-time output.

When the operations that the detection targets 411 carry out in the reference state have reached a predetermined number, when a predetermined period of time has elapsed, or when a predetermined amount of change occurs in the temperature of the first light detector 320, the switching member 611 is changed to the third state. The switching may be performed once every 100 times the first light detector 320 detects the second light L2 in the second state. Alternatively, the switching may be performed once every minute, or when the temperature of the first light detector changes ±0.2° C. or more with respect to the desired value. If the switching is to be performed in accordance with a temperature change, a temperature sensor for measuring the temperature of the first light detector 320 is required.

First Modification

The first modification of the present embodiment will be described below with reference to FIGS. 14A, 14B, and 14C.

The switch 609 is provided with a light shielding member 617 that shields at least one of the first light L1 and the second light L2, and a driver 615 that drives the light shielding member 617.

The light shielding member 617 may be a plate member. The material of the light shielding member 617 may be a metal such as copper or stainless steel. The light shielding member 617 may be configured to diffuse, absorb, or reflect the light. The light shielding member 617 is switched between the first state (see FIG. 14A), the second state (see FIG. 14B), and the third state (see FIG. 14C) by the driver 615. In the first state (see FIG. 14A), the light shielding member 617 is positioned between the light guide 601 and the first light detector 320 to shield the second light L2 only. In the second state (see FIG. 14B), the light shielding member 617 is positioned between the light guide 420 and the first light detector 320 to shield the first light L1 only. In the third state (see FIG. 14C), the light shielding member 617 is positioned between the light guide 601 and the first light detector 320 to shield the second light L2, and is also positioned between the light guide 420 and the first light detector 320 to shield the first light L1. In this manner, the light shielding member 617 selectively shields the first light L1 and the second light L2.

As shown in FIG. 14A, when the light shielding member 617 is switched to the first state, the first light L1 is guided to the first light detector 320 by the optical member 613, and is detected by the first light detector 320. Furthermore, the second light L2 is shielded by the light shielding member 617, and therefore will not be detected by the first light detector 320. As a result, the first light detector 320 functions in a manner similar to the first light detector 320 of the first embodiment. Accordingly, the first light detector 320 outputs the second change information.

As shown in FIG. 14B, when the light shielding member 617 is switched to the second state, the second light L2 is guided to the first light detector 320 by the optical member 613, and is detected by the first light detector 320. The first light L1 is shielded by the light shielding member 617, and therefore will not be detected by the first light detector 320. As a result, the first light detector 320 functions in a manner similar to the second light detector 603 of the first embodiment. Accordingly, the first light detector 320 outputs the first change information only. The main body 605 generates the suppression information.

As shown in FIG. 14C, when the light shielding member 617 is switched to the third state, the light shielding member 617 shields the first light L1 and the second light L2, and therefore neither the first light L1 nor the second light L2 is detected by the first light detector 320. In this manner, the first light detector 320 acquires a dark current (dark-time output). The light shield portion 611c can shield both the first light L1 and the second light L2 at the same time.

The light shielding member 617 is switched to the third state when the operations that the detection targets 411 carry out in the reference state have reached a predetermined number, when a predetermined period of time has elapsed, or when a predetermined amount of change occurs in the temperature of the first light detector 320.

In this modification, the light shielding member that shields only the first light L1 and the light shielding member that shields only the second light L2 may be separately provided.

Second Modification

A second modification of the present embodiment will be described below with reference to FIGS. 15A, 15B, and 15C.

The switch 609 is provided with a switching member 611, a light shielding member 617 that shields at least one of the first light L1 and the second light L2, and a driver 615 that drives the light shielding member 617. The switching member 611 is provided with a first transmission portion 611a through which the first light L1 is transmitted and a second transmission portion 611b through which the second light L2 is transmitted.

Figure 15C:
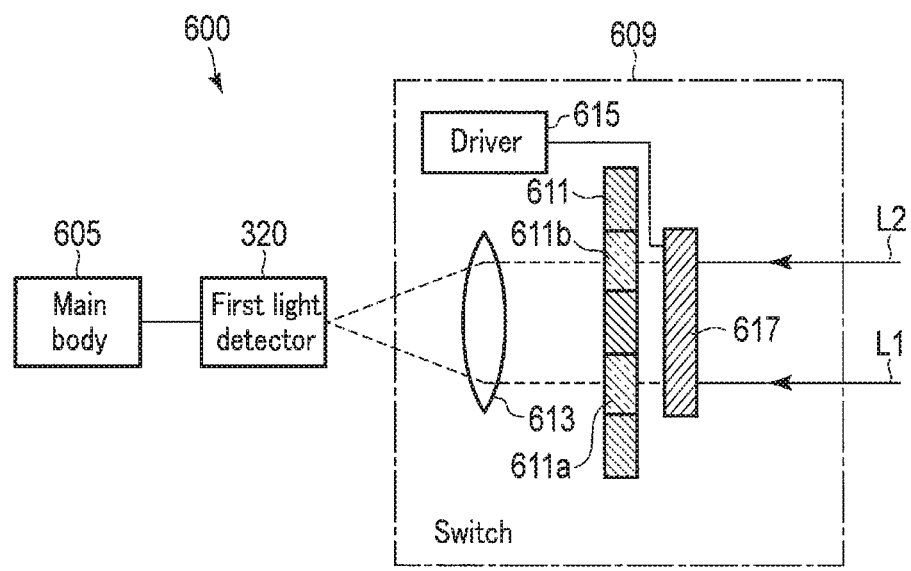
FIG. 15C is a diagram showing the light shielding member of FIG. 15A in the third state.

The light shielding member 617 is switched by the driver 615 to one of a first state (see FIG. 15A), a second state (see FIG. 15B), and a third state (see FIG. 15C). In the first state (see FIG. 15A), the light shielding member 617 is positioned between the second transmission portion 611b and the light guide 601 to shield only the second light L2. In the second state (see FIG. 15B), the light shielding member 617 is positioned between the first transmission portion 611a and the light branching element 330 to shield only the first light L1. In the third state (see FIG. 15C), the light shielding member 617 is positioned between the first transmission portion 611a and the light branching element 330, and between the second transmission portion 611b and the light guide 601 to shield the first light L1 and the second light L2. In this manner, the light shielding member 617 selectively shields the first light L1 and the second light L2.

In the first state shown in FIG. 15A, the first light L1 is transmitted through the first transmission portion 611a, guided to the first light detector 320 by the optical member 613, and detected by the first light detector 320. On the other hand, the second light L2 is shielded by the light shielding member 617, and is not detected by the first light detector 320. The first light detector 320 therefore functions in a manner similar to the first light detector 320 of the first embodiment. Accordingly, the first light detector 320 outputs the second change information.

In the second state shown in FIG. 15B, the second light L2 is transmitted through the second transmission portion 611b, guided to the first light detector 320 by the optical member 613, and detected by the first light detector 320. The first light L1 is shielded by the light shielding member 617, and is not detected by the first light detector 320. The first light detector 320 therefore functions in a manner similar to the second light detector 603 of the first embodiment. Accordingly, the first light detector 320 outputs the first change information only, and the main body 605 generates the suppression information.

In the third state shown in FIG. 15C, the light shielding member 617 shields the first light L1 and the second light L2, and therefore neither the first light L1 nor the second light L2 is detected by the first light detector 320. In this manner, the first light detector 320 acquires a dark current (dark-time output). The light shield portion 611c can shield both the first light L1 and the second light L2 at the same time.

The light shielding member 617 is switched to the third state when the operations that the detection targets 411 carry out in the reference state have reached a predetermined number, when a predetermined period of time has elapsed, or when a predetermined amount of change occurs in the temperature of the first light detector 320.

In this modification, the light shielding member that shields the first light L1 only and the light shielding member that shields the second light L2 only may be separately arranged.

Third Embodiment

Figure 16:
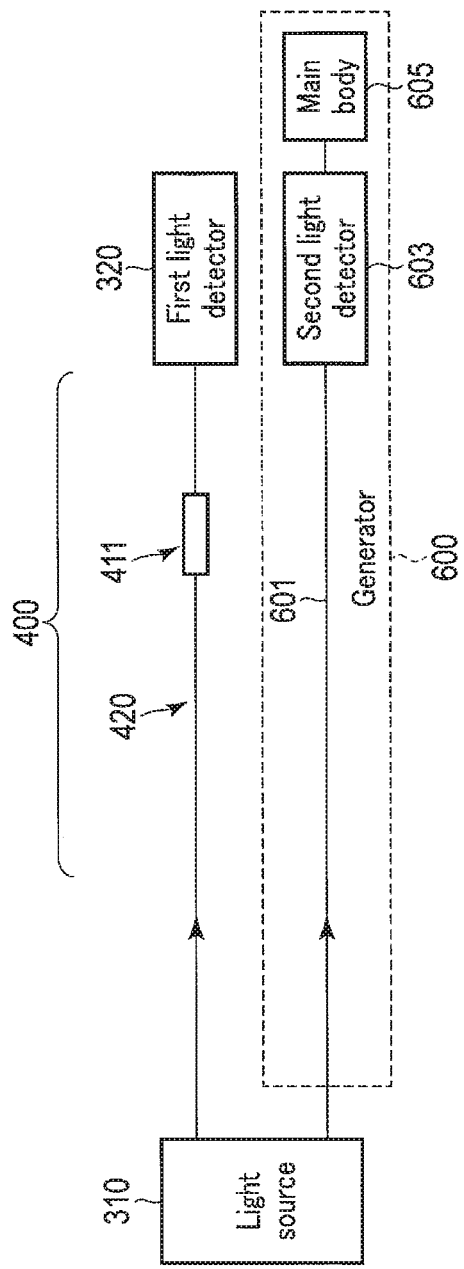
FIG. 16 is a block diagram showing an example configuration of the sensor according to the third embodiment.

A third embodiment will be described with reference to FIG. 16. According to the present embodiment, only portions different from the first embodiment will be described.

In the present embodiment, the light branching element 330 and the reflection member 430 are omitted. The light guide 420 is optically connected to the light source 310 at one end thereof, and optically connected to the first light detector 320 at the other end thereof.

Furthermore, according to the present embodiment, the light guide 601 is optically connected to the light source 310 at one end thereof, and optically connected to the second light detector 603 at the other end thereof. The light guide 601 is arranged parallel to the light guide 420.

According to the present embodiment, with the light branching element 330 and the reflection member 430 omitted, the loss of light attributed to these components can be reduced. In order to reduce the loss, the length of the sensor assembly 400 including the light guide 420 can be increased. The configuration according to this embodiment is therefore suitable for health monitoring of a structure that has an elongated installation length.

According to the present embodiment, it is preferable that the second light detector 603 be deposited in the vicinity of the first light detector 320, and the material of the light guide 601 be the same as the material of the light guide 420, and that the light guide 601 be disposed in the vicinity of the light guide 420. The loss of the light amount in the light guide 420 varies depending on the environment (e.g., temperature) in which the light guide 420 is installed. For this reason, a loss of the amount of light derived from the environment is created in both the light guide 420 and in the light guide 601, and these amounts of loss are approximately the same as each other. This means that the losses or the difference between these losses does not need to be taken into consideration in this embodiment.

Although it is not shown in the drawings, the second light detector 603 may be disposed in the vicinity of the light source 310. In such a structure, the length of the light guide 601 can be reduced, and the installation space can also be reduced.

According to this embodiment, only the first light detector 320 may be arranged by adopting the switch 609, as in the second embodiment.

Fourth Embodiment

Figure 17:
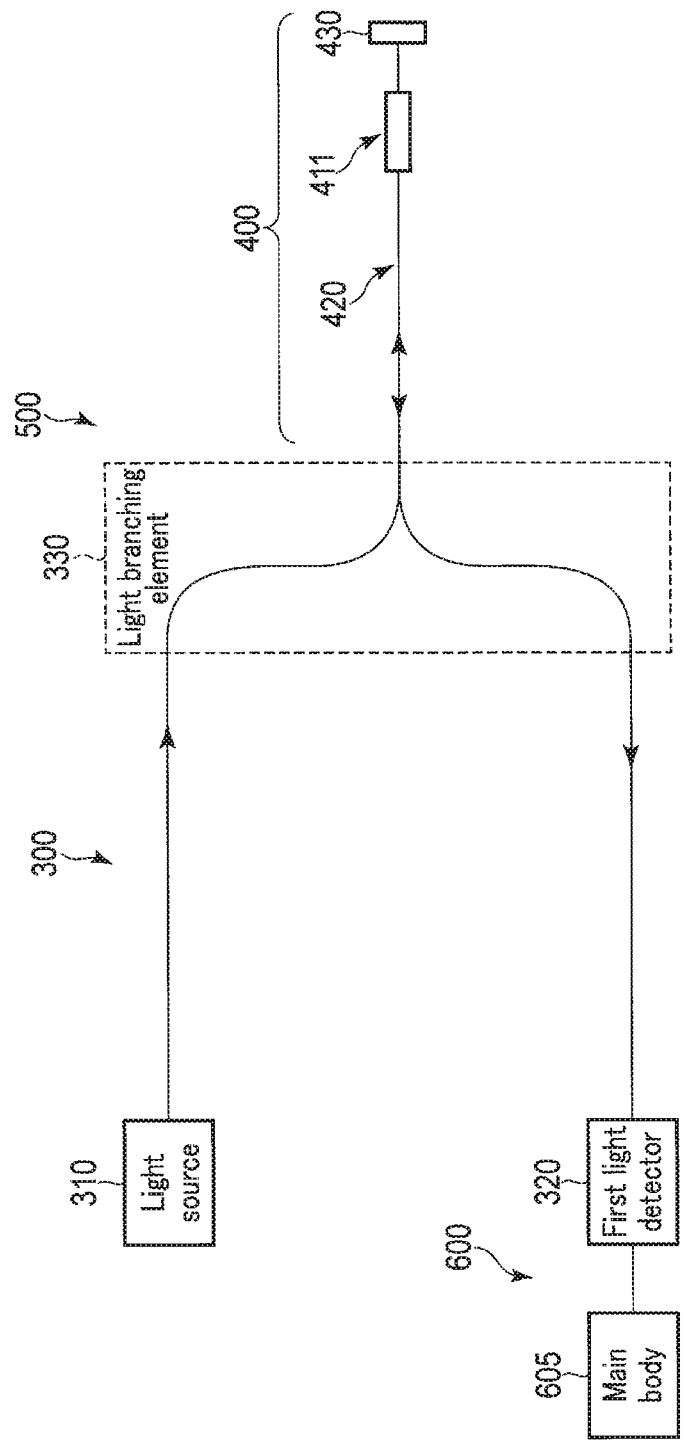
FIG. 17 is a block diagram showing an example configuration of the sensor according to the fourth embodiment.

The fourth embodiment will be described with reference to FIG. 17. According to the present embodiment, only portions different from the first embodiment will be described. The configuration of the present embodiment is substantially the same as the configuration of the first embodiment, but the procedure for calculating the third change information is different from that of the first embodiment. The second light detector 603 is omitted, and the generator 600 is provided with the first light detector 320 and the main body 605 that is connected to the first light detector 320.

At time T0, the detection targets 411 are in the reference state. In such a state, when the light having the first spectrum I0 is guided to the light guide 420, the first light detector 320 detects the first spectrum I0, and the light having the second spectrum Q0 is guided to the light guide 601.

At time T5, it is assumed that all the detection targets 411 are set to be in the known shapes, and that the first light detector 320 detects the first spectrum I5. If the spectrum of the light source 310 remains as the second spectrum Q0 at time T5, the bend change rate of the first spectrum is known, since the shapes of the detection targets 411 are already known. In other words, when the change of the spectrum of the light source 310 (first change information) is not considered, the bend change rate (third change information) is I5/I0.

If the spectrum of the light source 310 is changed to the second spectrum Q2 at time T5 and the first light detector 320 detects the first spectrum I5', the change rate (second change information) is I5'/I0.

Here, the change rate (second change information) at time T5 can be expressed as follows:

$$I5'/I0=(I5/I0)\times(Q2/Q0)$$

From this equation, the light source change rate (first change information (Q2/Q0)) can be obtained.

The time that is the same as time T4 in the example according to the first embodiment will be considered.

At time T6 that is approximately the same as time T4, all the detection targets 411 are set to the known shapes, and the first change information (Q6/Q0) is obtained. It is assumed here that the second spectrum Q6 at time T6 is equal to the second spectrum Q2 at time T4, which means that Q6/Q0=Q2/Q0.

The change rate at time T6 can be expressed as follows:

$$I6/I0=(I1/I0)\times(Q2/Q0)$$

According to the present embodiment, since the first change information (Q2/Q0) is known, the third change information (I1/I0) can be obtained. This eliminates the need to directly detect the specific second spectra Q0 and Q2, and Q6. Thus, the second light detector 603 of the first embodiment can be omitted, and the switch 609 of the second embodiment can be omitted.

The present invention is not limited to the above embodiments as is, but can be embodied in the implementation stage by modifying the structural components, without departing from the gist thereof. Various inventions can be created by suitably combining a plurality of structural components that are disclosed in the above embodiments.

What is claimed is:

1. A bend information computation apparatus comprising:
   a light source configured to emit light;
   a first light guide configured to guide first light which is part of the light;
   a detection target provided in the first light guide and having influence on a spectrum of the first light that is guided by the first light guide;
   a second light guide configured to guide second light which is part of the light and is different from the first light;
   a switching member including a first transmission portion having a predetermined first light transmittance, a second transmission portion having a second light transmittance different from the first light transmittance, and a light shield portion, wherein the first light guided by the first light guide and the second light guided by the second light guide travel to the switching member;
   a driver configured to drive the switching member and thereby switch between a first state and a second state, wherein, in the first state, the first transmission portion is positioned on an optical path of the first light to allow the first light to transmit through, and the light shield portion is positioned on an optical path of the second light to shield the second light; and in the second state, the light shield portion is positioned on the optical path of the first light to shield the first light, and the second transmission portion is positioned on the optical path of the second light to allow the second light to transmit through;
   a detector configured to detect a first spectrum change and a second spectrum change, wherein the first spectrum change is a change in the spectrum of the first light that has transmitted through the first transmission portion in the first state, and the second spectrum change is a change in a spectrum of the second light that has transmitted through the second transmission portion in the second state;
   a generator configured to calculate, based on the second spectrum change, suppression information to suppress influence of a change in a spectrum of the light source on the first spectrum change; and
   a bend information arithmetic operator configured to calculate change information based on the first spectrum change and the suppression information and to compute bend information representing a bend direction and a bend magnitude of the first light guide based on the change information, wherein the change information represents a spectrum change in which the influence of the change in the spectrum of the light source on the first spectrum change is suppressed.

2. The bend information computation apparatus according to claim 1, wherein, when operations that the detection targets carry out in the reference state have reached a predetermined number, when a predetermined period of time elapses, when a predetermined amount of change occurs in a temperature of the light source, or when an operation state of the light source changes, the detector detects the second spectrum change.

3. The bend information computation apparatus according to claim 1, wherein the second light transmittance of the second transmission portion is lower than the first light transmittance of the first transmission portion, and/or a second transmission spectrum of the second transmission portion is different from a first transmission spectrum of the first transmission portion.

4. The bend information computation apparatus according to claim 1, wherein, when the detection targets carry out in the reference state have reached a predetermined number, when a predetermined period of time elapses, or when a predetermined amount of change occurs in a temperature of the detector, the driver drives the switching member so as to switch the light shield portion to a third state in which the light shield portion shields the first light and the second light.

* * * * *